(12) United States Patent
Petkov et al.

(10) Patent No.: US 11,241,029 B2
(45) Date of Patent: Feb. 8, 2022

(54) THERMOSTABLE PHYTASES WITH HIGH CATALYTIC EFFICACY

(71) Applicant: HUVEPHARMA EOOD, Sofia (BG)

(72) Inventors: Spas Bojidarov Petkov, Plovdiv (BG); Nikolay Stoyanov Outchkourov, Bennekom (NL)

(73) Assignee: HUVEPHARMA EOOD, Sofia (BG)

( * ) Notice: Subject to any disclaimer, the term of this patent is extended or adjusted under 35 U.S.C. 154(b) by 0 days.

(21) Appl. No.: 16/123,806

(22) Filed: Sep. 6, 2018

(65) Prior Publication Data
US 2019/0069584 A1 Mar. 7, 2019

(30) Foreign Application Priority Data
Sep. 7, 2017 (EP) .................................. 17189861

(51) Int. Cl.
*A23L 29/00* (2016.01)
*C12N 15/70* (2006.01)
*C12N 9/16* (2006.01)
*A23K 20/189* (2016.01)

(52) U.S. Cl.
CPC ............ *A23L 29/06* (2016.08); *A23K 20/189* (2016.05); *C12N 9/16* (2013.01); *C12N 15/70* (2013.01); *C12Y 301/03008* (2013.01)

(58) Field of Classification Search
None
See application file for complete search history.

(56) References Cited

U.S. PATENT DOCUMENTS

| | | | |
|---|---|---|---|
| 3,297,548 | A | 1/1967 | Ware et al. |
| 9,528,096 | B1 | 12/2016 | Banerjee et al. |
| 9,605,245 | B1 | 3/2017 | Banerjee et al. |
| 10,351,832 | B2 * | 7/2019 | Banerjee ............... C12N 9/16 |
| 2010/0068335 | A1 | 3/2010 | Lei |
| 2015/0132383 | A1 | 5/2015 | Solbak et al. |

FOREIGN PATENT DOCUMENTS

| | | |
|---|---|---|
| WO | WO 94/03612 | 2/1994 |
| WO | WO 99/67398 | 12/1999 |
| WO | WO 01/36607 | 5/2001 |
| WO | WO 03/37102 | 5/2003 |
| WO | WO 03/057247 | 7/2003 |
| WO | WO 2006/042719 | 4/2006 |
| WO | WO2009/073399 | 6/2009 |
| WO | WO2015/197871 | 12/2015 |

OTHER PUBLICATIONS

Hayashi et al. (DNA Res., vol. 8, 2001, pp. 11-22).*
European Search Report prepared for EP17189861.2, completed Nov. 23, 2017.
Database Accession No. AWW34521, "*Escherichia coli*/Maize Phytase (Nov9X) Mutant Mut24 Protein SEQ ID:111." 2009.
Garrett, James B., et al., "Enhancing the Thermal Tolerance and Gastric Performance of a Microbial Phytase for Use as a Phosphate-Mobilizing Monogastric-Feed Supplement," 2004, Applied and Environmental Microbiology, vol. 70, No. 5, pp. 3041-3046.
Lei, Xin Gen, et al., "Phytase, A New Life for an "Old" Enzyme," 2013, vol. 1, No. 1, pp. 283-309.
Database Accession No. BCK62300, "*Escherichia coli*Mature Varient Phytase, SEQ: 6." 2016.
Cosgrove, "Inositol Phosphate Phosphatases Of Microbiological Origin. Inositol Phosphate Intermediates In The Dephosphorylation Of The Hexaphosphates Of Myo-Inositol, Scyllo-Inositol, and $_D$-chiro-inositol by a bacterial (*Pseudomonas* SP.) Phytase," Aust. J. Biol. Sci., 23:1207-1220 (1970).
Genbank Accessioin No. AAA72086.1 (1990).
Kim et al. "An improved method for a rapid determination of phytase activity in animal feed," J. Animal Sci., 83(5): 1062-1067 (May 2005).
Nayini et al., "The Phytase of Yeast," Lebensm.-Wiss. u.—Technol., 17(1): 24-26 (1984).
Nelson et al., "Effect of Supplemental Phytase on the Utilization of Phytate Phosphorus by Chicks," J. Nutrition, 101: 1289-1294 (1971).
Powar et al., "Purification and Properties of Phytate-Specific Phosphatase from *Bacillus subtilis*,"J. Bacteriology, 151(3): 1102-1108 (Sep. 1982).
Studier, "Protein production by auto-induction in high-density shaking cultures," Protein Expression and Purification 41: 207-234 (2005).
Yamada et al., "Phytase from *Aspergillus terreus*; Part I. Production, Purficiation and Some General Properties of the Enzyme," Agr. Biol. Chem., 32(10): 1275-1282 (1968).

* cited by examiner

*Primary Examiner* — Hope A Robinson
(74) *Attorney, Agent, or Firm* — Barnes & Thornburg LLP

(57) ABSTRACT

The present invention provides phytase enzymes exhibiting a surprisingly high thermostability as compared to commercially available phytases. Additionally some of the new phytase variants display up to four fold increased catalytic rate thus greatly increased speed of phytate dephosphorilation.

30 Claims, 8 Drawing Sheets

Specification includes a Sequence Listing.

THERMOSTABLE PHYTASES WITH HIGH CATALYTIC EFFICACY

CROSS-REFERENCE TO RELATED APPLICATIONS

This application claims the benefit of European Patent Application Serial Number 17189861.2, filed on Sep. 7, 2017, the entire disclosure of which is incorporated herein by reference.

The present invention provides phytase enzymes exhibiting a surprisingly high thermostability as compared to commercially available phytases. Variants with improved catalytic activity are also disclosed.

BACKGROUND

Phytases are enzymes releasing inorganic phosphate from phytate. Phytases are used as feed additives to increase release of inorganic phosphorus from phytate in the feed. Commercial phytases currently used in the industry are supposed to have high catalytic efficacy, stability in the stomach of monogastric animals and a high thermostability in order to retain most of their activity after heat treatment during feed pelleting.

Minerals are essential elements for the growth of all organisms. For livestock production of monogastric animals (e.g., pigs, poultry) and fish, feed is commonly supplemented with minerals. Plant seeds are a rich source of minerals since they contain ions that are complexed with the phosphate groups of phytic acid. Ruminants do not require inorganic phosphate and minerals because microorganisms in the rumen produce enzymes that catalyze conversion of phytate (myo-inositol-hexaphosphate) to inositol and inorganic phosphate. In the process, minerals that have been complexed with phytate are released.

Phytate occurs as a source of stored phosphorous in virtually all plant feeds (Phytic Acid, Chemistry and Applications, E. Graf (Ed.), Pilatus Press: Minneapolis, Minn., U.S.A., 1986). Phytic acid forms a normal part of the seed in cereals and legumes. It functions to bind dietary minerals that are essential to the new plant as it emerges from the seed. When the phosphate groups of phytic acid are removed by the seed enzyme phytase, the ability to bind metal ions is lost and the minerals become available to the plant. In livestock feed grains, the trace minerals bound by phytic acid are only partially available for absorption by monogastric animals, which lack phytase activity. Although some hydrolysis of phytate occurs in the colon, most phytate passes through the gastrointestinal tract of monogastric animals and is excreted in the manure contributing to fecal phosphate pollution problems in areas of intense livestock production. Inorganic phosphorous released in the colon has no nutritional value to livestock because inorganic phosphorous is absorbed only in the small intestine. Thus, a significant amount of the nutritionally important dietary minerals are potentially not available to monogastric animals.

Conversion of phytate to inositol and inorganic phosphorous can be catalyzed by microbial enzymes referred to broadly as phytases. Phytases are capable of catalyzing hydrolysis of myo-inositol hexaphosphate to D-myo-inositol pentaphosphate and orthophosphate. Based on catalytic mode of action there are two types of phytases, a 3-phytase (EC.3.1.3.8) removes phosphate groups at the 1 and 3 positions of the myo-inositol ring, and a 6-phytase (EC.3.1.3.6) which first releases the phosphate at the 6-position of the ring. Certain fungal phytases reportedly hydrolyze inositol pentaphosphate to tetra-, tri-, and lower phosphates; e.g., *A. ficuum* phytases reportedly produce mixtures of myoinositol di- and mono-phosphate (Ullah, 1988). Phytase producing microorganisms comprise bacteria such as *Bacillus subtilis* (V. K. Powar and V. J. Jagannathan, J. Bacteriol. 151:1102-1108, 1982) and *Pseudomonas* (D. J. Cosgrove, Austral. J. Biol. Sci. 2:1207-1220, 1970); yeasts such as *Sacchoromyces cerevisiae* (N. R. Nayini and P. Markakis, Lebensmittel Wissenschaft und Technologie 17:24-26, 1984); and fungi such as *Aspergillus terreus* (K. Yamada, et al., Agric. Biol Chem. 32:1275-1282, 1968). The possible use of microbes capable of producing phytase as a feed additive for monogastric animals has been reported previously (Shieh and Ware, U.S. Pat. No. 3,297,548; Nelson, T. S. et al., J. Nutrition 101:1289-1294, 1971).

Microbial phytases may also reportedly be useful for producing animal feed from certain industrial processes, e.g., wheat and corn waste products. The wet milling process of corn produces glutens sold as animal feeds. Addition of phytase may reportedly improve the nutritional value of the feed product.

A particular class of 6-phytases are encoded by appA genes from *E. coli*. First appA gene (Gene bank: AAA72086.1), to be cloned and sequenced was initially recognized as pH 2.5 acid phosphatase (Dassa et al., 1990). With the cloning of the second appA2 gene (Gene bank: AAR87658.1) and its overproduction in yeast Rodriguez and coworkers (Rodriguez et al., 1999) have provided direct evidence that appA enzymes are rather phytases than acid phosphatases. AppA and appA2 contain six amino acids differences, namely S102P, P195S, S197L, K202N, K298M, and T299A in the coding region of their mature protein (Rodriguez et al., 1999). However both appA and appA2 encode active 6-phytases (WO2003037102A3 and WO1999067398A3) and thus both appA and appA2 proteins are natural variants of the *E. coli* 6-phytase. Currently the number of appA gene encoded variants deposited in the database is about 450. Many of the deposited appA proteins contain combination variants in the six amino acids different between the appA and appA2 in their coding region.

Other appA enzyme variants have been generated in the laboratory with the aim of achieving improved enzyme properties such as intrinsic thermostability, enzyme kinetics or increased productivity of appA 6-phytases in their production hosts (Rodriguez et al 2000; WO2001036607A1; WO 2006042719 A3; WO 2003037102 A2; WO 2006042719 A3; WO 2003057247 A1).

AppA phytase variants have been produced in yeast systems such as *Pichia pastoris* (a.k.a. *Komagataella phaffii*) (Lee 2005; WO 1999067398 A9) and *Trichoderma reesei* (WO 1994003612 A1).

AppA2C is identical to appA2 (AAR87658.1) with the exception of amino acids 195P, 197S. The last two are identical to appA (AAA72086.1). The sequence of appA2C is shown herein as SEQ ID NO: 1. Appa2C is thus a hybrid of appA and appA2 with naturally present amino acid variations.

The overall object underlying the present invention is the provision of appA2C variants which exhibit an improved thermostability as compared to appA2C. Preferably these variants keep the same enzyme characteristics, such as broad pH optimum and fast enzyme kinetics. It is furthermore an object underlying the present invention to provide appA2C variants exhibiting a thermostability comparable to or higher than the phytases disclosed in WO 2003057247 A1 and US2015132383A1. Thus, the new appA2C thermostable variants are compared with two commercially available phytases, i.e. OptiPhos and Quantum Blue 5G, both of which are based on the appA gene variants from *E. coli*. The new appA2C thermostable variants shall preferably have a higher or at least comparable thermostability than these phytases.

SUMMARY OF THE INVENTION

It has been surprisingly found by the present inventors that specific variants of appA2C exhibit a drastically improved thermostability compared to OptiPhos. These variants exhibit particular mutations, namely at least at positions 4, 62, 137, 159, 185, 211, 255 and 327 of SEQ ID NO: 1 (appA2C).

A first sub-variant with a surprisingly improved thermostability is the variant denominated PhOP-0093 (SEQ ID NO: 2). This variant was found to exhibit an improved thermostability compared to appA2C in that it retains 50% thermostability at a temperature which is 13.5° C. higher than for appA2C (50% thermostability at 79.5° C. versus 66° C.) when expressed in *E. coli*; and which is 20° C. higher than for appA2C (50% thermostability at 86° C. versus 66° C.) when expressed in *Pichia pastoris*.

The thermostability of PhOP-0093 (i.e. the phytase having the amino acid sequence of SEQ ID NO: 2) is comparable to the thermostability of Quantum Blue 5G (50% thermostability at 89° C.).

It was furthermore surprisingly found by the present inventors that certain further mutations in SEQ ID NO: 2 are responsible for an even higher thermostability. Variants exhibiting mutations at positions 4, 62, 137, 159, 185, 211, 255 and 327 of SEQ ID NO: 1 (appA2C), preferably retaining the amino acids E4, W62, V137, Y159, N185, W211, D255 and Y327 of SEQ ID NO: 2, exhibit thermostability even if further variations within SEQ ID NO: 2 are made to create variants of SEQ ID NO: 2. Accordingly, the present invention provides:

1. A phytase selected from
   a) a polypeptide comprising the amino acid sequence of SEQ ID NO: 2 [sequence of PhOP-0093],
   b) a variant of the polypeptide comprising the amino acid sequence of SEQ ID NO: 2 which
      (i) retains the following amino acid positions E4, W62, V137, Y159, N185, W211, D255 and Y327 of SEQ ID NO: 2 and preferably includes one or more additional mutations at positions 35, 73, 107, 139, 157, 176, 179, 227, 253, 287.
      (ii) contains one or more substitutions at positions other than E4, W62, V137, Y159, N185, W211, D255 and Y327 of SEQ ID NO: 2,
   c) a variant of the polypeptide comprising the amino acid sequence of SEQ ID NO: 2 which
      (i) retains the following amino acid positions E4, W62, V137, Y159, N185, W211, D255 and Y327 of SEQ ID NO: 2, and
      (ii) exhibits a sequence identity of at least 90% with SEQ ID NO: 2, preferably 95%, more preferably 98%, most preferably 99%;
   d) a variant of the protein comprising the amino acid sequence of SEQ ID NO: 2 which
      (i) retains the following amino acid positions E4, W62, V137, Y159, N185, W211, D255 and Y327 of SEQ ID NO:2, and
      (ii) contains one or more amino acid substitutions, additions or deletions compared to SEQ ID NO: 2.
   Preferably, the present invention provides a phytase selected from
   d') a variant of the protein comprising the amino acid sequence of SEQ ID NO: 2 which
      (i) retains the following amino acid positions E4, W62, V137, Y159, N185, W211, D255 and Y327 of SEQ ID NO:2, and
      (ii) contains one or more amino acid substitutions, additions or deletions compared to SEQ ID NO: 2,
      wherein the variant contains between one and ten, one and five, preferably one and three amino acid substitutions, and/or between one and ten, one and five, preferably one and three amino acid additions and/or between one and ten, one and five, preferably one and three amino acid deletions compared to SEQ ID NO: 2.
      in a most preferred embodiment, the variant contains between one and three amino acid substitutions, and/or between one and three amino acid substitutions and/or between one and three amino acid deletions compared to SEQ ID NO: 2.
   e) a protein exhibiting one or more substitutions, additions or deletions compared to SEQ ID NO: 2.
   Preferably, the present invention provides a phytase selected from
   e') a protein exhibiting one or more substitutions, additions and/or deletions compared to SEQ ID NO: 2.
   wherein the protein contains between one and ten, one and five, preferably one and three amino acid substitutions, and/or between one and ten, one and five, preferably one and three amino acid additions or between one and ten, one and five, preferably one and three amino acid deletions compared to SEQ ID NO: 2.
   in a most preferred embodiment, the variant contains between one and three amino acid substitutions, and/or between one and three amino acid substitutions and/or between one and three amino acid deletions compared to SEQ ID NO: 2.
2. The phytase of embodiment 1 which exhibits a thermostability of 50% at 75° C., 80° C., 85° C., 90° C., 95° C. or 100° C.
3. The phytase of embodiment 1 or 2 which exhibits a thermostability of 70% at 75° C., 80% at 75° C., 85% at 75° C., 90% at 75° C., or 95% at 75° C.
4. The phytase of any of embodiments 1-3 which exhibits a thermostability of 50% at 95° C., 55% at 95° C., 60% at 95° C., 65% at 95° C., 80% at 80° C., 80% at 85%, or 80% at 90° C.
5. The phytase of any of embodiments 1-4 selected from a polypeptide comprising the amino acid sequence of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

6. The phytase of embodiment 1b) wherein the one or more additional mutations are selected from 35Y, 73P, 107G, 139R, 157R/S/N, 176P, 179K, 227E, 253Y and 287S in SEQ ID NO: 2.
7. The phytase of embodiment 6, wherein one or more additional mutations are at positions 25, 43 and/or 225, preferably 25F, 43P and/or 225Y.
8. The phytase of any of embodiments 1-7 which is expressed in a fungal host cell, preferably a yeast host cell.
9. The phytase of any of embodiments 1-7 which is expressed in a bacterial host cell, preferably E. coli.
10. A nucleic acid sequence encoding any of the phytases of any of embodiments 1-7.
11. A vector comprising the nucleic acid of embodiment 10.
12. A host cell comprising the nucleic acid of embodiment 10 or the vector of embodiment 11.
13. The host cell of embodiment 12, which is a fungal host cell, preferably a yeast host cell, or a bacterial host cell, preferably E. coli.
14. Use of a phytase of any of embodiments 1-7 for releasing phosphate from phytate.
15. The use of a phytase of any of embodiments 1-7 as a feed ingredient.
16. A method of preparing a phytase of any of embodiments 1-7 by recombinantly expressing the enzyme in a host cell according to embodiment 12 or 13.
17. Use of a phytase of any of embodiments 1-7 for increasing or improving the feed conversion rate.
   The feed conversion rate (FCR) is the ratio of feed input (in kg) to bodyweight gain obtained after feeding (in kg).
   Preferably, the phytase in embodiment 17 comprises one of the amino acid sequences of SEQ ID NOs:3 or 6. More preferably, the phytase is PhOP-0136 or PhOP-0161.
18. Use of a phytase of any of embodiments 1-7 for improving the content of available phosphate in animal feed.
   The percentage of ash (ash mainly consists of calcium and phosphate) in the bones such as tibia is a measure for available dietary phosphorous in feeding stuffs.
   Preferably, the phytase in embodiment 18 comprises one of the amino acid sequences of SEQ ID NOs:3 or 6. More preferably, the phytase is PhOP-0161 or PhOP-0136.
19. Use of a phytase of any of embodiments 1-7 for improving the average daily weight gain.
   The average daily gain (ADG) is the average gain of body weight per day in animals. Preferably, the phytase in embodiment 19 comprises the amino acid sequence of SEQ ID NO:6. More preferably, the phytase is PhOP-0161.

DETAILS OF THE INVENTION

Figure 1:
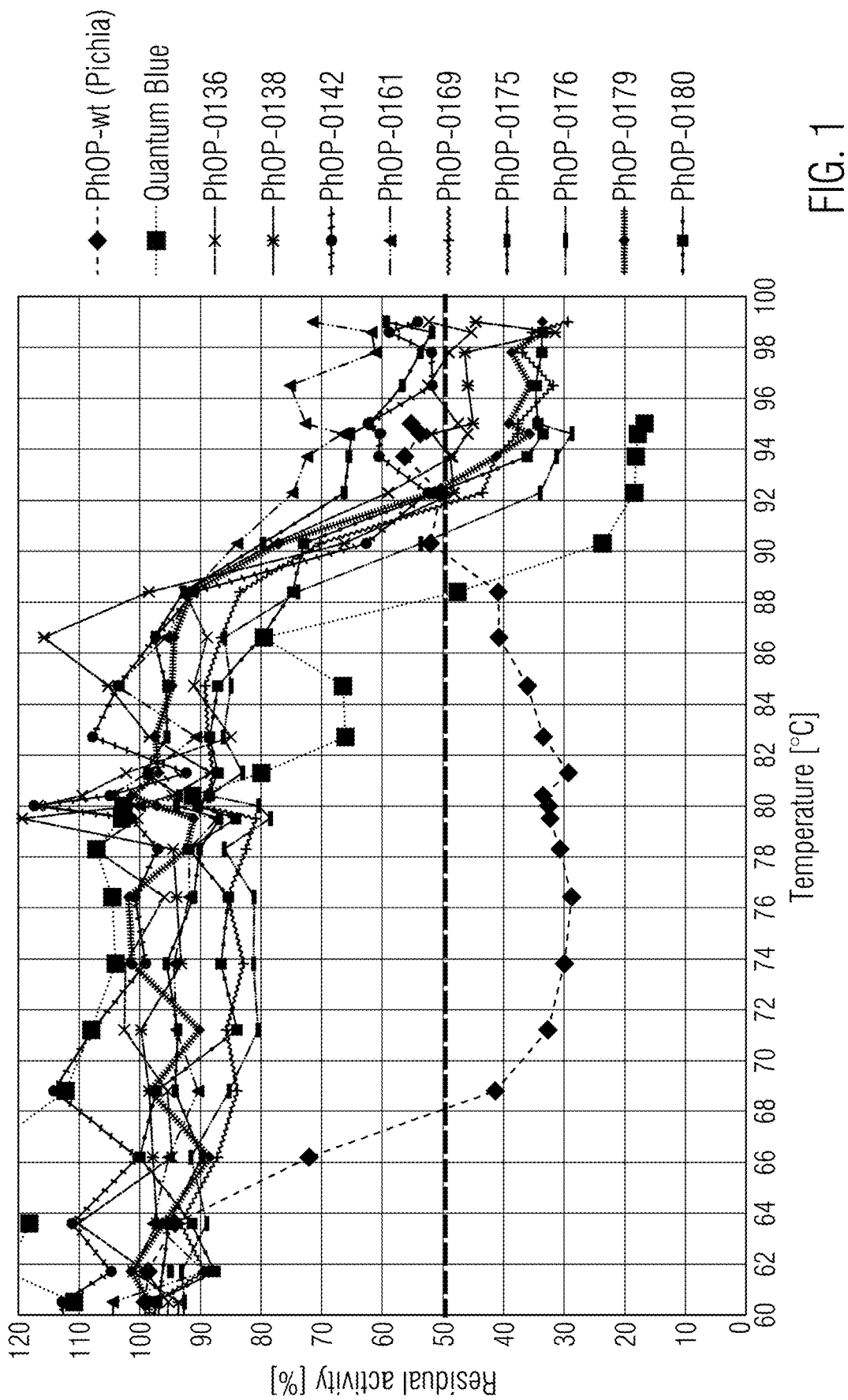
FIG. 1 shows thermostability profiles of nine embodiments of the present invention expressed in Pichia in comparison to PhOP-wt (appA2C) and the commercially available phytase Quantum Blue 5G.

The present invention provides phytase variants with an increased thermostability compared to appA2C or likewise compared to OptiPhos. The variants are denominated PhOP-variants ("phytase *Escherichia coli*" variants). Some explicit variants are shown in SEQ ID NOs: 2-11. The numbering of amino acids in these variants follows the numbering of SEQ ID NO: 1 (appA2C), which corresponds to the numbering of the wild type phytase appA2 (AAR87658.1) as published in Rodriguez et al., 1999. AppA2 and appA2C encompass 432 amino acids including a native signal sequence (22 amino acids) followed by the mature phytase sequence (410 amino acids). The native signal sequence is shown in SEQ ID NO: 12.

The phytase variants of the present invention exhibit excellent thermostability. "Thermostability" is determined by measuring the residual phytase enzymatic activity at a temperature of 37° C. (body temperature) after having heated the phytase enzyme for 15 minutes to a certain temperature followed by a subsequent cooling to 37° C. The reference enzymatic activity is determined after exposing the enzyme for 15 minutes to 25° C. and subsequently measuring the enzymatic activity at 37° C. By comparing to this later enzymatic activity, the relative activity is calculated.

The 50% thermostability ("TM50 value") is the temperature where an enzyme retains 50% of its activity after a heat treatment. TM50 values are indicative for the evaluation and comparison of enzyme thermostability.

AppA gene variants can be expressed in any eukaryotic or prokaryotic expression system. Preferably, the appA phytase variants are produced in *E. coli* and *Pichia pastoris* after codon usage optimization. Preferably the synthetic gene variants encoding PhOP-variant phytases are cloned into plasmids for expression in *E. coli* using a strong promoter such as the T7 promoter or in *P. pastoris* using a strong promoter such as AOX. To achieve secretion into the periplasm (*E. coli*) or the medium (*Pichia*) the native signal sequence (*E. coli*, 22 amino acids long) or the alfa mating factor (*Pichia*, 89 amino acids long) were used as N-terminal signal sequences and fused to the appA2C mature protein.

Preferably PhOP-phytase variants are expressed in *E. coli* in shake flasks or in 96-well plates. A preferred promoter is the strong T7 promoter. Preferably precultures containing one single clone per well are incubated overnight. After harvesting, the cells are lysed by subjecting the cell suspension to three freezing-thawing cycles in lysis buffer (100 mM sodium citrate buffer (pH 5.5), 2 mM $MgCl_2$, 0.5 mg/ml lysozyme, 20 U/ml NuCLEANase). Crude cell extracts are obtained after centrifugation and collection of the supernatants upon separation from the cell debris.

Preferably, the enzymatic activity of phytases is determined by screening assays as follows: Phytases are expressed in host cells, preferably *E. coli* or *Pichia pastoris* host cells. Enzyme extracts from *E. coli* or *Pichia pastoris* are incubated for 15 minutes at the temperature chosen for the heat step as well as room temperature (reference) following incubation on ice and centrifugation. Afterwards the phytase activities are determined at 37° C. (body temperature). Enzymatic activities of phytase in 96 well plates is performed by adaptation of the method of Kim and Lei, J. Anim. Sci. 2005. 83:1062-1067.

The phosphate released from phytate by a 2-step procedure is determined photometrically:

1st Step: Release of Pi from Phytate by Phytase

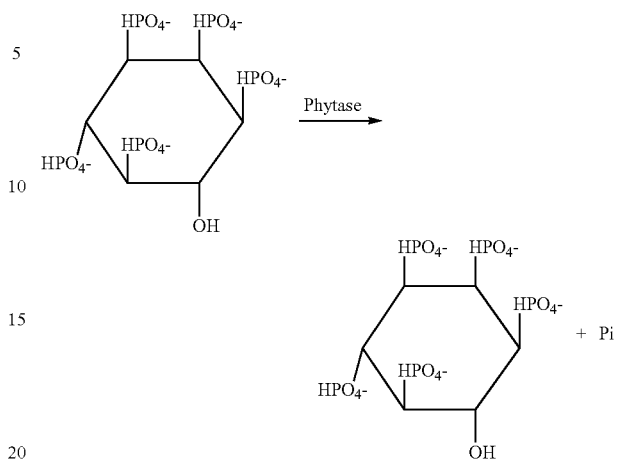

2nd Step: Determination of PI (as Phosphomolybdate Complex)

Scheme 1: reaction scheme of phytase activity assay

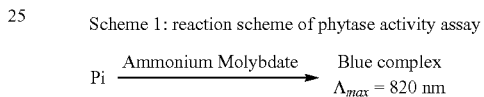

Table 1 depicts 9 explicit variants (SEQ ID NOs: 3-11) together with SEQ ID NO: 2 (PhOP-0093). These variants exhibit extraordinary thermostability.

TABLE 1

Nine explicit appa2C variants (SEQ ID NOs. 3-11) compared to appA2C. These variants exhibit extraordinary thermostability.

| | Position (*) | | | | | | | | | | | | | | | | | |
|---|---|---|---|---|---|---|---|---|---|---|---|---|---|---|---|---|---|---|
| | 26 | 57 | 84 | 95 | 129 | 159 | 161 | 179 | 181 | 198 | 201 | 207 | 233 | 249 | 275 | 277 | 309 | 349 |
| PhOP-wt (AppA2c) | P | D | Q | A | D | N | N | G | R | N | L | D | V | Q | Q | Y | Q | T |
| PhOP-0093 | E | D | W | A | D | V | N | G | Y | N | L | N | W | Q | Q | D | Q | Y |
| PhOP-0136 | E | Y | W | P | G | V | R | G | Y | P | K | N | W | E | Y | D | S | Y |
| PhOP-0138 | E | Y | W | P | G | V | R | N | Y | P | K | N | W | Q | Y | D | S | Y |
| PhOP-0142 | E | Y | W | P | D | V | R | N | Y | P | K | N | W | E | Y | D | Q | Y |
| PhOP-0161 | E | Y | W | P | D | V | N | S | Y | P | K | N | W | E | Y | D | S | Y |
| PhOP-0169 | E | Y | W | A | G | V | R | S | Y | P | K | N | W | E | Y | D | S | Y |
| PhOP-0175 | E | Y | W | P | D | V | R | N | Y | N | K | N | W | E | Y | D | S | Y |
| PhOP-0176 | E | D | W | P | G | V | R | N | Y | P | K | N | W | Q | Y | D | S | Y |
| PhOP-0179 | E | Y | W | P | G | V | R | N | Y | P | L | N | W | E | Y | D | S | Y |
| PhOP-0180 | E | Y | W | P | G | V | R | N | Y | P | K | N | W | E | Y | D | S | Y |

SEQ ID NO:2 is the sequence of PhOP-0093, SEQ ID NO:3 is the sequence of PhOP-0136, SEQ ID NO:4 is the sequence of PhOP-0138, SEQ ID NO:5 is the sequence of PhOP-0142, SEQ ID NO:6 is the sequence of PhOP-0161, SEQ ID NO:7 is the sequence of PhOP-0169, SEQ ID NO:8 is the sequence of PhOP-0175, SEQ ID NO:9 is the sequence of PhOP-0176, SEQ ID NO:10 is the sequence of PhOP-0179, SEQ ID NO:11 is the sequence of PhOP-0180.

It was surprisingly identified that the mutations at position 4, 62, 137, 159, 185, 211, 255 and 327 of appA2C (SEQ ID NO: 1) are essential to the increase in thermostability. While other mutations or changes in the amino acid sequence are possible, or even beneficial, these 8 mutations of the appA2C sequence, resulting in PhOP-0093 (with mutations 4E, 62W, 137V, 159Y, 185N, 211 W, 255 D and 327Y relative to SEQ ID NO:1) were key to the improvement in the thermostability. Thermostability is increased, if the phytases are expressed in bacterial cells, preferably *E. coli* (see Table 2).

TABLE 2

Thermostability (TM50 values) of phytases expressed in *E. coli*. Thermostability profiles were determined after heating for 15 minutes to the respective temperatures; relative activity was determined as compared to "heating" for 15 minutes to 25° C.

| Phytase variants expressed in *E. coli* | 57 | 95 | 129 | 161 | 179 | 198 | 201 | 249 | 275 | 309 | Activity relative to PhOP-0093 | Tm50 [° C.] | Improvement to OptiPhos [° C.] |
|---|---|---|---|---|---|---|---|---|---|---|---|---|---|
| PhOP-0093 | D | A | D | N | G | N | L | Q | Q | Q | 100% | 79.5 | 13.5 |
| PhOP-0122 | D | A | D | N | G | N | L | Q | Y | Q | 88% | 82.0 | 16.0 |
| PhOP-0136 | Y | P | G | R | G | P | K | E | Y | S | 53% | 88.0 | 22.0 |
| PhOP-0138 | Y | P | G | R | N | P | K | Q | Y | S | 75% | 87.5 | 21.5 |
| PhOP-0142 | Y | P | D | R | N | P | K | E | Y | Q | 97% | 88.0 | 22.0 |
| PhOP-0161 | Y | P | D | N | S | P | K | E | Y | S | 72% | 87.5 | 21.5 |
| PhOP-0169 | Y | A | G | R | S | P | K | E | Y | S | 62% | 89.5 | 23.5 |
| PhOP-0175 | Y | P | D | R | N | N | K | E | Y | S | 75% | 88.5 | 22.5 |
| PhOP-0176 | D | P | G | R | N | P | K | Q | Y | S | 101% | 87.5 | 21.5 |
| PhOP-0179 | Y | P | G | R | N | P | L | E | Y | S | 74% | 88.5 | 22.5 |
| OptiPhos | | | | | | | | | | | | 66.0 | 0.0 |
| QuantumBlue 5G | | | | | | | | | | | | 89.0 | 23.0 |
| PhOP-0093 (*Pichia*) | | | | | | | | | | | | 86.0 | 20.0 |
| PhOP-wt (*E. coli*) | | | | | | | | | | | | 63.0 | −3.0 |
| PhOP-wt (*Pichia*) | | | | | | | | | | | | 67.0 | 1.0 |

TABLE 3

Thermostability of phytases in *Pichia pastoris* (TM50 values). Thermostability profiles were determined after heating for 15 minutes to the respective temperatures; relative activity was determined with reference to "heating" for 15 minutes to 25° C.

| Phytase variants expressed in *Pichia pastoris* | Tm50 [° C.] | Improvement to OptiPhos [° C.] |
|---|---|---|
| Opti Phos | 66.0 | 0.0 |
| QuantumBlue 5 G | 89.0 | 23.0 |
| PhOP-wt | 67.0 | 1.0 |
| PhOP-0093 | 86.0 | 20.0 |
| PhOP-0136 | 93.8 | 27.8 |
| PhOP-0138 | 92.3 | 26.3 |
| PhOP-0142 | 93.3 | 27.3 |
| PhOP-0161 | >99 | 33.0 |
| PhOP-0169 | 91.5 | 25.5 |
| PhOP-0175 | 99.0 | 33.0 |
| PhOP-0176 | 90.5 | 24.5 |
| PhOP-0179 | 92.3 | 26.3 |
| PhOP-0180 | 92.5 | 26.5 |

Phytases expressed in yeast host cells instead of bacterial host cells exhibit an even higher thermostability. This is shown in Table 3. All variants exhibit a thermostability comparable to or higher than Quantum Blue 5G. Raw data is shown in FIG. 1.

Further variants of PhOP-0093 exhibiting a surprisingly high thermostability are shown below.

Some of the phytase variants of the invention have the amino acid sequences of phytase variants of SEQ ID NOs: 2-11. All phytase variants of the invention are characterized by catalyzing the hydrolysis of phytate to inositol and free phosphate with the release of minerals from the phytic acid complex and having an improved thermostability.

Also included in the invention are polypeptides having sequences that are "substantially identical" to the sequence of a phytase polypeptide. A "substantially identical" amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Fragments of the phytase variants of the present invention retain at least one phytase-specific activity or epitope. Phytase activity can be assayed by examining the conversion of phytate to inositol and free phosphate.

For example, a fragment containing, e.g., at least 8-10 amino acids can be used as an immunogen in the production of phytase-specific antibodies. In addition to their use as peptide immunogens, the above-described phytase fragments can be used in immunoassays, such as ELISAs, to detect the presence of phytase-specific antibodies in samples.

Other phytase variants included in the invention are variants having amino acid sequences that exhibit a sequence identity of at least 90% with SEQ ID NO: 2, preferably 95%, more preferably 98%, most preferably 99%.

The length of the amino acid sequence for determining amino acid sequence identity can be, for example, at least 20 amino acids, for example, at least 25, or 35 amino acids. Preferably, the length of the amino acid sequence for determining amino acid sequence identity, is 400 amino acids, more preferably 410 amino acids, most preferably 432 amino acids. Identity can be measured using standard sequence analysis software (e.g., Sequence Analysis Software Package of the Genetics Computer Group, University of Wisconsin Biotechnology Center, 1710 University Avenue, Madison, Wis. 53705; also see Ausubel, et al., supra). Such procedures and algorithms include, for example, a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignmnet by Genetic ALgorithm) and WHAT-IF.

The phytase polypeptides of the invention can be obtained using a recombinant expression system (see below), chemically synthesized (this approach may be more suitable for small phytase peptide fragments), or purified from organisms in which they are naturally expressed.

The invention also provides isolated nucleic acid molecules that encode the phytase polypeptides described above. For example, nucleic acids that encode any of SEQ ID NOs:2-11 are included in the invention. These nucleic acids can contain naturally occurring nucleotide sequences, or degenerated sequences still encoding the same amino acid sequence. The nucleic acid sequences of the invention can contain DNA or RNA nucleotides, or combinations or modifications thereof.

The present invention also relates to vectors which include nucleic acid sequences of the present invention, host cells which are genetically engineered to include the vectors of the invention and the production of enzymes of the invention by recombinant techniques.

Host cells are genetically engineered (transduced or transformed or transfected) with the vectors containing the nucleic acid sequences of this invention. Such vectors may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those appropriate for the host cell selected for expression, and will be apparent to the ordinarily skilled artisan.

The nucleic acid sequences of the present invention may be employed for producing enzymes by recombinant techniques. Thus, for example, the nucleic acid sequence may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate nucleic acid sequence may be inserted into the vector by a variety of procedures. In general, the DNA sequence is inserted into an appropriate restriction endonuclease site(s) by procedures known in the art. Such procedures and others are deemed to be within the knowledge of those skilled in the art.

The nucleic acid sequence in the expression vector is operatively linked to an appropriate expression control sequence(s) (promoter) to direct mRNA synthesis. As representative examples of such promoters, there may be mentioned: LTR or SV40 promoter, the E. coli. lac or tip, the phage lambda $P_L$ promoter and other promoters known to control expression of genes in prokaryotic or eukaryotic cells or their viruses. The expression vector may also contain a ribosome binding site for translation initiation and a transcription terminator. The vector may also include appropriate sequences for amplifying expression.

In addition, the expression vector preferably contains one or more selectable marker genes to provide a phenotypic trait for selection of transformed host cells such as dihydrofolate reductase, zeocin or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the polypeptide.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells adenoviruses; plant cells, etc. The selection of an appropriate host is deemed to be within the knowledge of those skilled in the art from the teachings herein. Preferred host cells are bacterial and fungal host cells. More preferred are yeasts, including, for example, Saccharomyces, Kluyveromyces, Torulaspora, Schizosaccharomyces, Pichia, Hansenula, Torulopsis, Candida, and Karwinskia species. The yeast can be a methylotrophic strain, e.g., strains of Pichia, Hansenula, Torulopsis, Candida, and Karwinskia. As noted above, the host cell can be a non-yeast cell. Non-yeast cells of particular interest include, for example, Aspergillus species, Trichoderma species, Neurospora species, Myceliopthora species, Penicillium species, Bacillus species and Lactococcus species.

The recombinant phytases can be produced by using intracellular expression, or by extracellular secretion into the cell culture media.

Host cells are typically harvested by centrifugation, disrupted by physical or chemical means, and the resulting crude extract retained for further purification.

Host cells employed in expression of enzymes can be disrupted by any convenient method, including freeze-thaw cycling, sonication, mechanical disruption, or use of cell lysing agents, such methods are well known to those skilled in the art.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a purified natural product, or a product of chemical synthetic procedures, or obtained by recombinant techniques from a prokaryotic or eukaryotic host (for example, by bacteria, yeast, higher plant, insect or mammalian cells in culture). Depending upon the host employed in a recombinant production procedure, the enzymes of the present invention may be glycosylated or may be non-glycosylated.

Enzymes of the invention may or may not also include an initial methionine amino acid residue.

The enzyme of this invention may be employed for any purpose in which such enzyme activity is necessary or desired. In a preferred embodiment the enzyme is employed for catalyzing the hydrolysis of phytate. The degradation of phytate may be beneficial in animal feed.

Examples

1 General Methods and Analytics 1.1 Expression in E. coli and Preparation of PhOP-Wildtype and Variants in a Screening Procedure (Microtiter Plate (MTP) Format Expression of PhOP- in E. coli: E. coli BL21(DE3) cells transformed with plasmid pLE1A17 (derivative of pRSF-1b, Novagen) carrying the PhOP-gene with its native N-terminal signal sequence was cultivated in ZYM5052 medium (F. William Studier, Protein Expression and Purification 41 (2005) 207-234) supplemented with kanamycin (50 mg/i) and grown overnight at 30° C. Cells were harvested and lysed by three freezing-thawing cycles in lysis buffer (100 mM sodium citrate buffer, pH 5.5, 2 mM $MgCl_2$, 0.5 mg/ml lysozyme, 20 U/ml NuCLEANase (c-LEcta GmbH)). Crude cell extracts were obtained after centrifugation and collection of the supernatants from cell debris.

1.2 Determination of Volumetric Activity of Phytase

The general principle is a photometrical determination of Pi released from phytate by a two-step reaction as shown in Scheme 1.

1st Step: Release of Pi from Phytate by Phytase

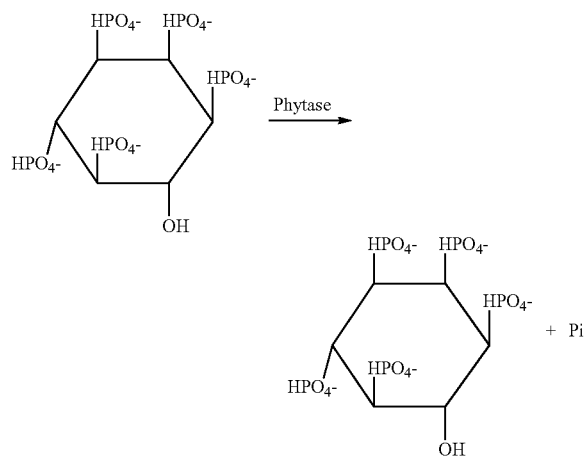

2nd Step: Determination of Pi (as Phosphomolybdate Complex)

Scheme 1: reaction scheme of phytase activity assay

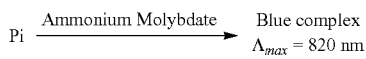

Inorganic phosphate (Pi) was released from phytate by action of phytase in a buffer composed of 1% (w/v) phytate, 0.2 M sodium citrate, pH 5.5. After incubation at 37° C. for 30 minutes phytase reactions were stopped by addition of 1 volume of 15% trichloracetic acid (TCA). Blank assay controls for determination of potential phosphate contamination of phytase samples were taken along by mixing phytase samples with 15% TCA and afterwards with the substrate buffer. In the second step the Pi released during phytase reaction was determined by complexation with ammonium molybdate. The stopped reaction assays were diluted 10 fold with $H_2O$ and 75 µl of the diluted samples were mixed with 75 µl of complexing Reagent (0.5% ammonium molybdate, 0.6 M sulfuric acid, 2% ascorbic acid). After incubation for 60 minutes at 37° C. the absorption at a wavelength of 820 nm was measured. Quantification was done by comparison to a phosphate calibration curve.

By this method the Pi concentration could be determined very accurately over a broad range. In a preferred embodiment, phytase activity is determined for phytase expressed in E. coli and in Pichia pastoris.

1.3 Determination of Tm50-Values (Thermostability)

The Tm50-value was defined as the temperature where an enzyme retains 50% of its activity after a heat treatment and is therefore indicative for the evaluation and relevant for comparison of an enzyme's thermostability. Samples containing phytase were subjected to heat treatments at temperatures ranging between 58-99° C. for 15 min and were compared to a sample incubated at 25° C. for normalization of residual activities. After a regeneration step for 30 minutes on ice and centrifugation to remove precipitated protein, the volumetric activities in the samples were determined using the screening assay described in section 1.2. By plotting residual activities against incubation temperatures the Tm50-values were derived from these graphs.

1.4 Subcloning and Expression of PhOP-Variants in Pichia

The genes of variants selected by screening in the E. coli system were subcloned into Pichia expression plasmid pLE3B06 under the control of the AOX-Promotor. To achieve secretion into the medium the native N-terminal signal sequence used in the E. coli system was replaced by the alpha-mating factor signal sequence. Transformation of the P. pastoris strain LE3A100 was done with the linearized pLE3B06-PhOP-construct. Positive transformation clones were selected by supplementing Pichia standard medium YPD with 100 µg/ml zeocin. PhOP-clones were precultured in shaking flasks in BMGY medium overnight at 30° C. Expression was done in Pichia standard medium BMMY after methanol induction of the AOX promoter. BMGY and BMMY media are described in Pichia expression kit K1710-01 manual from ThermoFisher Scientific. BMMY cultures were inoculated with 1/30 volume of BMGY precultures. Each 24 h expression culture was fed by addition of 0.5% (v/v) of the inducer methanol. Expression was performed for 72 h followed by centrifugation and recovery of the culture supernatants. In order to remove the phosphate present in the BMMY standard medium the supernatants were rebuffered into 0.2 M sodium citrate buffer (pH 5.5) before activity determination. Rebuffering was done using PD-10 Columns from GE Healthcare following the manufacturer's protocol.

2. Engineering of PhOP

An approach for improving performance of enzymes and their suitability for use in industrial processes is enzyme engineering. This technique involves developing variants of a starting enzyme with improved properties (for review, see, for example, S. Lutz, U. T. Bomscheuer, Protein Engineering Handbook, Wiley VCH, Weinheim, 2009). Variant libraries of PhOP-were created and screened in E. coli with the methods described in 1.1 and 1.2. The template enzyme for the enzyme engineering was PhOP-0093 (SEQ ID NO: 2)

In the general enzyme engineering strategy, phytase variants with individual aminoacids mutations were screened and beneficial mutations were subsequently recombined together to generate new libraries.

Firstly, in a screening of a variant library of PhOP-0093 a series of enzyme variants with improved thermostability were identified (Table 4).

TABLE 4

Activity data of variants tested

| Mutation in PhOP-0093 | Mutant | Activity relative to PhOP-0093 | Residual activity (81.2° C. 15 min) |
|---|---|---|---|
| — | PhOP-0093 | 100% | 4% |
| D57Y | PhOP-0097 | 54% | 9% |
| G74Y | PhOP-0099 | 17% | 16% |
| G74S | PhOP-0098 | 55% | 9% |
| A95P | PhOP-0100 | 125% | 15% |
| D112H | PhOP-0101 | 34% | 8% |
| D112S | PhOP-0102 | 20% | 8% |
| E113Q | PhOP-0103 | 55% | 13% |
| A121F | PhOP-0104 | 65% | 9% |
| D129G | PhOP-0105 | 86% | 22% |
| A131D | PhOP-0106 | 42% | 6% |
| N161R | PhOP-0107 | 130% | 15% |
| N161Q | PhOP-0109 | 108% | 15% |
| N161A | PhOP-0108 | 125% | 9% |
| T163R | PhOP-0110 | 123% | 9% |
| D164A | PhOP-0111 | 97% | 8% |
| D164R | PhOP-0112 | 68% | 6% |
| G179S | PhOP-0115 | 71% | 14% |
| G179N | PhOP-0113 | 70% | 8% |
| G179H | PhOP-0114 | 86% | 6% |
| T183E | PhOP-0116 | 58% | 8% |
| N198P | PhOP-0117 | 83% | 14% |
| L201K | PhOP-0118 | 61% | 9% |
| Q249E | PhOP-0119 | 77% | 17% |
| S262D | PhOP-0120 | 61% | 6% |
| T267L | PhOP-0121 | 49% | 8% |
| Q275F | PhOP-0124 | 26% | 29% |
| Q275Y | PhOP-0122 | 80% | 27% |
| Q275V | PhOP-0123 | 20% | 21% |
| Q309S | PhOP-0126 | 63% | 16% |
| Q309Y | PhOP-0125 | 88% | 7% |
| Q309G | PhOP-0127 | 66% | 6% |
| E337D | PhOP-0129 | 61% | 6% |
| A402H | PhOP-0130 | 44% | 7% |

Further recombining individual mutations and library screening yielded a series of variants with significantly improved thermostability and containing various combinations of amino acid exchanges in positions 35, 73, 107, 139, 157, 176, 179, 227, 253, and 287 (Table 5).

TABLE 5

Very promising variants: the 20 most stable variants among those tested

| Variant | 57 | 95 | 129 | 161 | 179 | 198 | 201 | 249 | 275 | 309 | Activity relative to PhOP-0093 | Residual activity 88° C. | Residual activity 89° C. | Residual activity 90° C. | Residual activity 91° C. | Thermo-Profile |
|---|---|---|---|---|---|---|---|---|---|---|---|---|---|---|---|---|
| PhOP-0093 | D | A | D | N | G | N | L | Q | Q | Q | 100% | 0% | 0% | 0% | 0% | x |
| PhOP-0122 | D | A | D | N | G | N | L | Q | Y | Q | 88% | 0% | 1% | 0% | 0% | x |
| PhOP-0136 | Y | P | G | R | G | P | K | E | Y | S | 53% | 39% | 45% | 49% | 20% | x |
| PhOP-0179 | Y | P | G | R | N | P | L | E | Y | S | 74% | 42% | 44% | 46% | 11% | x |
| PhOP-0169 | Y | A | G | R | S | P | K | E | Y | S | 62% | 48% | 54% | 40% | 8% | x |
| PhOP-0142 | Y | P | D | R | N | P | K | E | Y | Q | 97% | 40% | 39% | 36% | 7% | x |
| PhOP-0131 | Y | P | G | R | G | N | K | E | Y | S | 64% | 35% | 44% | 33% | 6% | x |
| PhOP-0163 | Y | A | G | R | N | P | K | E | Y | Q | 65% | 40% | 49% | 30% | 5% | x |
| PhOP-0175 | Y | P | D | R | N | N | K | E | Y | S | 75% | 47% | 36% | 29% | 2% | x |
| PhOP-0138 | Y | P | G | R | N | P | K | Q | Y | S | 75% | 52% | 49% | 28% | 5% | x |
| PhOP-0139 | D | P | G | R | N | N | K | E | Y | S | 64% | 40% | 46% | 25% | 4% | x |
| PhOP-0137 | Y | A | G | R | S | N | L | E | Y | S | 60% | 42% | 35% | 20% | 1% | |
| PhOP-0143 | Y | P | G | R | N | N | K | E | Y | Q | 43% | 45% | 36% | 18% | 1% | |
| PhOP-0161 | Y | P | D | N | S | P | K | E | Y | S | 72% | 39% | 25% | 15% | 1% | x |
| PhOP-0176 | D | P | G | R | N | P | K | Q | Y | S | 101% | 36% | 31% | 14% | 1% | x |
| PhOP-0171 | Y | A | G | R | S | P | L | E | Y | Q | 72% | 42% | 31% | 13% | 1% | |
| PhOP-0133 | Y | A | D | R | N | N | K | E | Y | S | 55% | 42% | 33% | 13% | 0% | |
| PhOP-0152 | D | P | D | R | N | P | K | E | Y | Q | 90% | 38% | 30% | 12% | 1% | |
| PhOP-0145 | Y | P | D | R | S | P | L | E | Y | Q | 65% | 36% | 29% | 12% | 1% | |
| PhOP-0135 | Y | A | G | N | N | P | L | E | Y | S | 63% | 33% | 31% | 12% | 0% | |
| PhOP-0146 | Y | P | G | N | N | P | K | E | Y | Q | 75% | 29% | 31% | 10% | 0% | |
| PhOP-0170 | Y | A | G | N | N | N | K | E | Y | S | 64% | 38% | 29% | 10% | 0% | |

Figure 2:
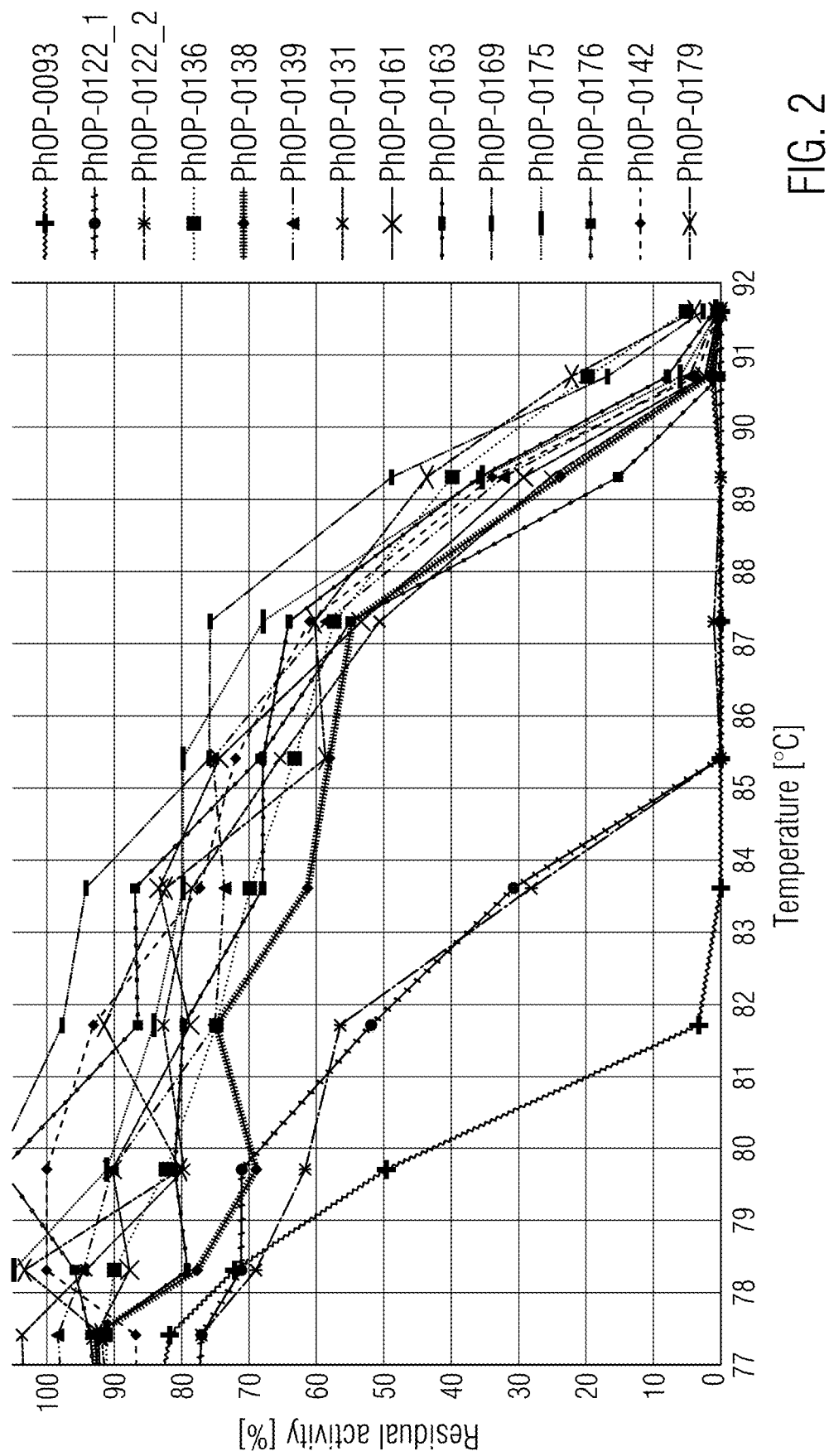
FIG. 2 shows thermostability profiles of eleven embodiments of the present invention expressed in E. coli in comparison to PhOP-0093 and PhOP-0122.

For a selection of eleven variants (marked in right column in Table 5) thermostability profiles were generated to determine Tm50-values in comparison with PhOP-0093 and PhOP-0122 (FIG. 2). Thermostability profiles revealed improvements of Tm50-values by recombination of beneficial mutations between ~6-8° C. over the most stable variant PhOP-0122 from mutant libraries or ~8-10° C. in comparison to PhOP-0093. Taking into account the stability improvement of PhOP-0093 (from *E. coli*) over OptiPhos reference by 13.5° C., recombination variants from *E. coli* are between 21.5-23.5° C. more stable than the OptiPhos reference. Data are shown in Table 6.

Variants prepared from *Pichia* were expected to be even more stable than variants expressed in *E. coli*. Accordingly, eight variants tested in *E. coli* and an additionally ninth variant (PhOP-0180) carrying beneficial mutations in all 10 positions were chosen for subsequent sub-cloning and expression in *Pichia* according to section 1.4. The thermostability of these variants are shown in Table 7 and FIG. 1.

improved by 4.5 to 13° C. Consequently, all final variants show higher thermostability than the commercially available phytase Quantum Blue 5G. The most stable variants PhOP-0161 and PhOP-0175 are at least ~10° C. more stable than Quantum Blue 5G. The variants expressed and glycosylated by *Pichia* are more stable than enzymes from *E. coli* and they do not get completely inactivated at high temperatures but retain rather high residual activities of 30% and higher (e.g. PhOP-0161 with ~60% residual activity after 99° C. incubation).

3. New Thermostable Variants with Increased Catalytic Rate of Phytate Diphosphorylation Four of the new highly thermostable phytase variants were expressed in *Pichia pastoris*, and purified to homogeneity. Their Michaelis-Menten kinetics were studied in great detail at conditions similar to the monogastric animal's digestive tract: i.e. at pH 2-4 and a temperature of 39° C.

TABLE 6

Preferred embodiments of the invention expressed in *E. coli*

| Phytase variants expressed in *E. coli* | 57 | 95 | 129 | 161 | 179 | 198 | 201 | 249 | 275 | 309 | Activity relative to PhOP-0093 | Tm50 [° C.] | Improvement to OptiPhos [° C.] |
|---|---|---|---|---|---|---|---|---|---|---|---|---|---|
| PhOP-0093 | D | A | D | N | G | N | L | Q | Q | Q | 100% | 79.5 | 13.5 |
| PhOP-0122 | D | A | D | N | G | N | L | Q | Y | Q | 88% | 82.0 | 16.0 |
| PhOP-0136 | Y | P | G | R | G | P | K | E | Y | S | 53% | 88.0 | 22.0 |
| PhOP-0138 | Y | P | G | R | N | P | K | Q | Y | S | 75% | 87.5 | 21.5 |
| PhOP-0142 | Y | P | D | R | N | P | K | E | Y | Q | 97% | 88.0 | 22.0 |
| PhOP-0161 | Y | P | D | N | S | P | K | E | Y | S | 72% | 87.5 | 21.5 |
| PhOP-0169 | Y | A | G | R | S | P | K | E | Y | S | 62% | 89.5 | 23.5 |
| PhOP-0175 | Y | P | D | R | N | N | K | E | Y | S | 75% | 88.5 | 22.5 |
| PhOP-0176 | D | P | G | R | N | P | K | Q | Y | S | 101% | 87.5 | 21.5 |
| PhOP-0179 | Y | P | G | R | N | P | L | E | Y | S | 74% | 88.5 | 22.5 |
| OptiPhos | | | | | | | | | | | | 66.0 | 0.0 |
| QuantumBlue 5G | | | | | | | | | | | | 89.0 | 23.0 |
| PhOP-0093 (*Pichia*) | | | | | | | | | | | | 86.0 | 20.0 |
| PhOP-wt (*E. coli*) | | | | | | | | | | | | 63.0 | −3.0 |
| PhOP-wt (*Pichia*) | | | | | | | | | | | | 67.0 | 1.0 |

TABLE 7

Preferred embodiments of the invention expressed in *P. pastoris*

| Phytase variants expressed in *Pichia pastoris* | Tm50 [° C.] | Improvement to OptiPhos [° C.] |
|---|---|---|
| OptiPhos | 66.0 | 0.0 |
| QuantumBlue 5 G | 89.0 | 23.0 |
| PhOP-wt | 67.0 | 1.0 |
| PhOP-0093 | 86.0 | 20.0 |
| PhOP-0136 | 93.8 | 27.8 |
| PhOP-0138 | 92.3 | 26.3 |
| PhOP-0142 | 93.3 | 27.3 |
| PhOP-0161 | >99 | 33.0 |
| PhOP-0169 | 91.5 | 25.5 |
| PhOP-0175 | 99.0 | 33.0 |
| PhOP-0176 | 90.5 | 24.5 |
| PhOP-0179 | 92.3 | 26.3 |
| PhOP-0180 | 92.5 | 26.5 |

Figure 3:
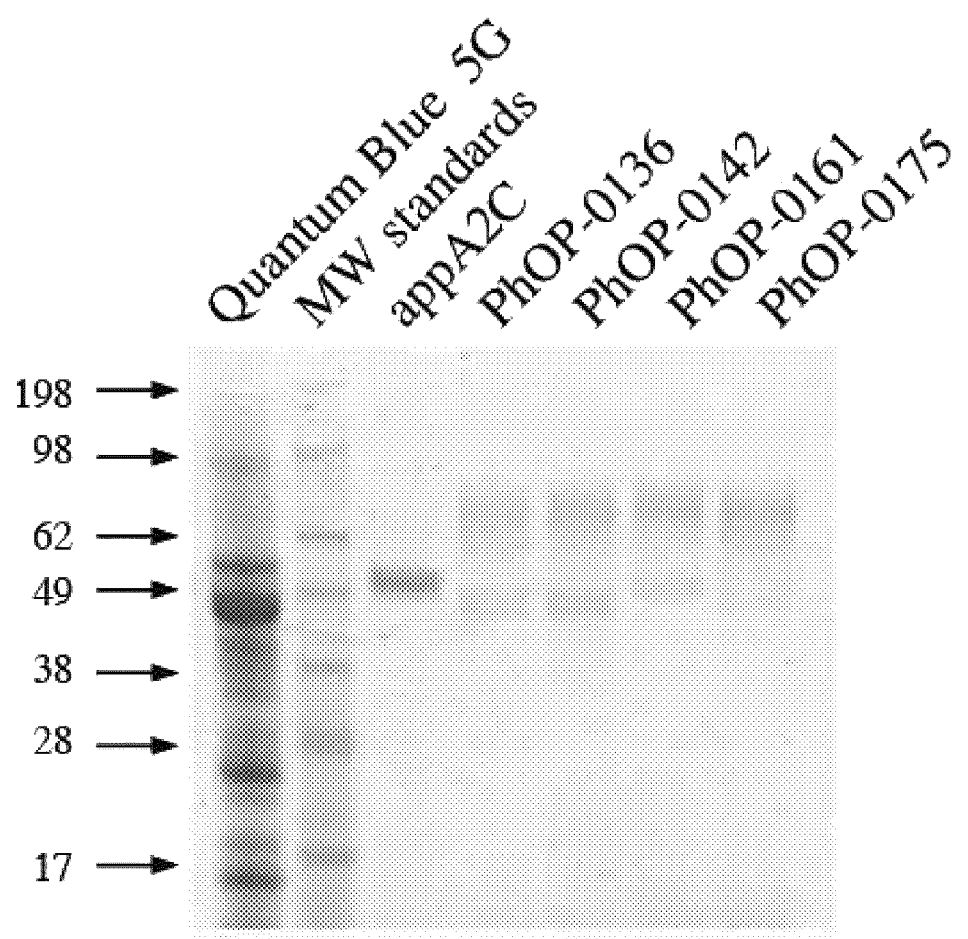
FIG. 3 shows SDS-PAGE analysis of supernatants from Pichia pastoris producing appA2C, PhOP-0136, PhOP-0142, PhOP-0161, PhOP-0175 and Quantum Blue 5G.

A comparison of the thermostability profiles (FIG. 1) revealed highly improved stabilities compared to the OptiPhos reference for all of the final PhOP-variants generated. The thermostability increase by 24.5 to >33° C. is shown by enhanced Tm50-values. In comparison to the template variant PhOP-0093 the thermostability was further FIG. 3 shows SDS-PAGE analysis of *Pichia pastoris* supernatants producing appA2C, PhOP-0136, PhOP-0142, PhOP-0161, PhOP-0175 and Quantum Blue 5G commercial product.

Recombinant proteins were purified using combination of conventional chromatography and ultrafiltration and their enzymatic properties were analyzed in in vitro kinetic studies using phytate as substrate.

Figure 4:
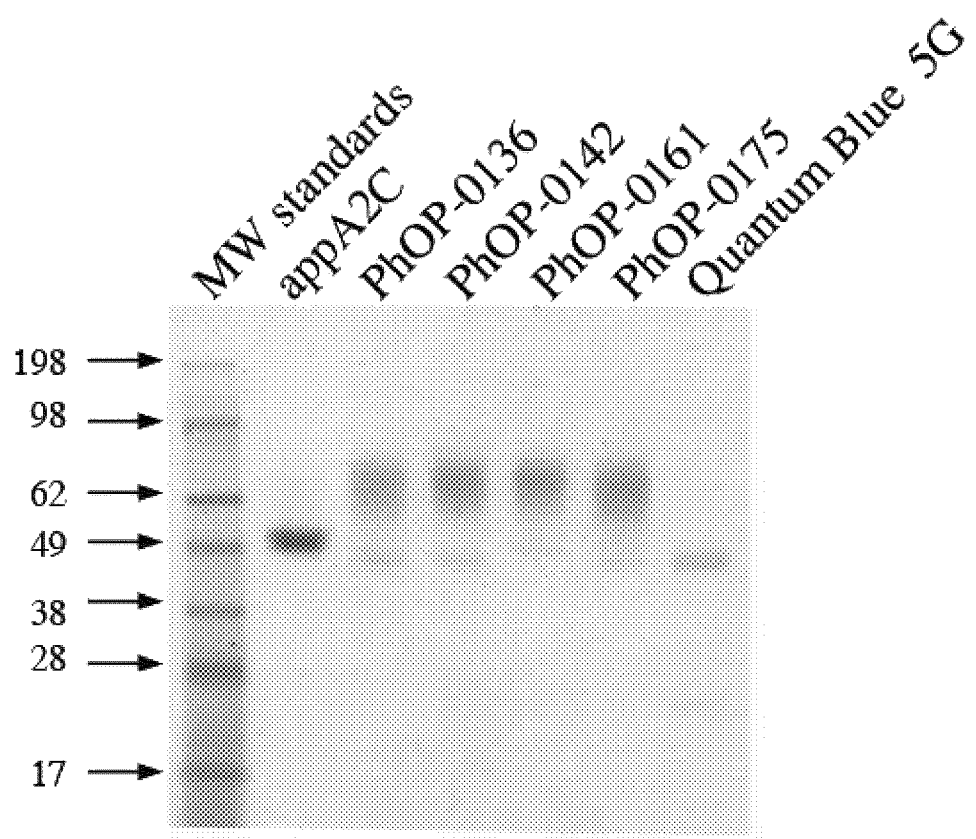
FIG. 4 shows SDS-PAGE analysis of purified phytases: appA2C, PhOP-0136, PhOP-0142, PhOP-0161, PhOP-0175 and Quantum Blue 5G.
Figure 5:
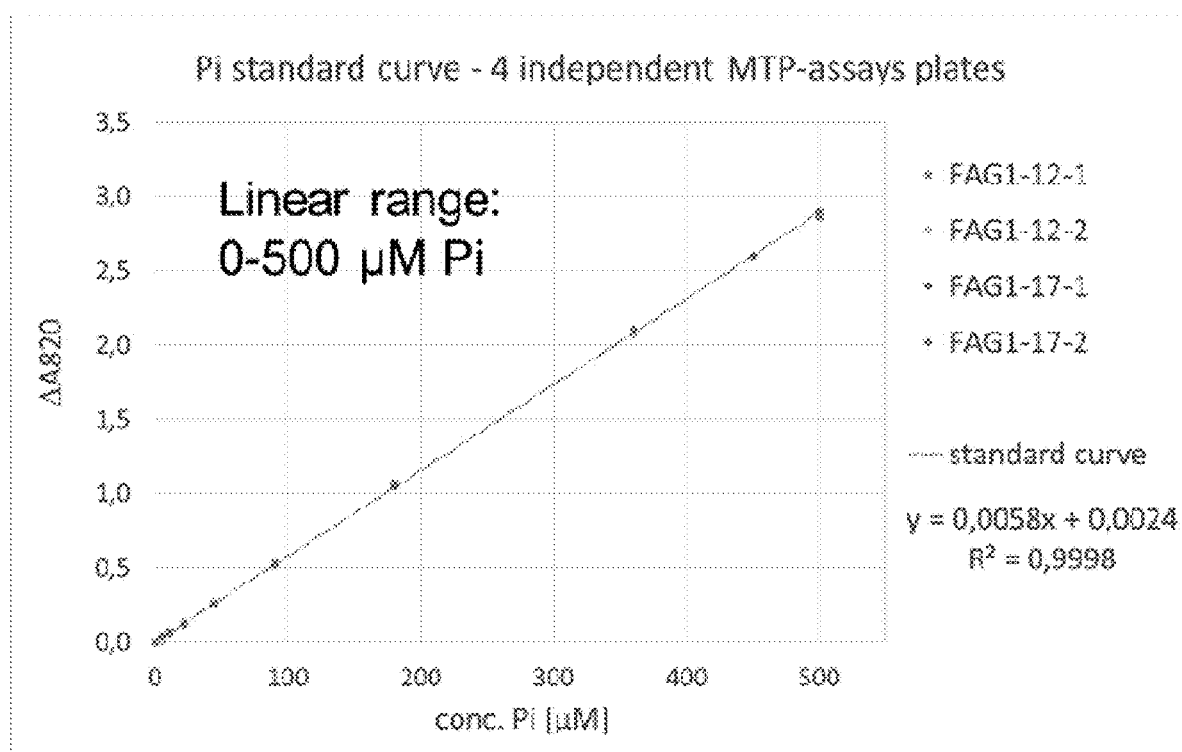
FIG. 5 shows a calibration curve correlating the inorganic phosphate concentration $P_i$ with the absorbance at 820 nm, $A_{820}$. Data points of four different microtiter assay plates ("Fag 1-12-1", "Fag 1-12-2", "Fag 1-17-1", "Fag 1-17-2") are included.

FIG. 4 shows SDS-PAGE analysis of purified phytases: appA2C, PhOP-0136, PhOP-0142, PhOP-0161, PhOP-0175 and Quantum Blue 5G.

4. Determination of Kinetic Parameters

Different kinetic parameters for phytate hydrolysis were determined in Glycine-HCl reaction buffer at pH range 2.0-4.0 and temperature 39° C., both relevant for the animal (poultry and pigs) digestive tract. The Km and Vmax values for different phytase preparations were calculated from Lineweaver-Burk plot using substrate concentrations ranging from 0.02-0.17 mM.

A variant PhOP-0136 was identified to be particularly interesting as it displayed a high catalytic rate Kcat against phytate in addition to its high thermostability. A variant PhOP-0161 was also interesting as it possessed high Kcat/Km ratio indicating combination of higher substrate specificity and catalytic efficiency a.k.a. catalytic perfection (Berg, J. M., Tymoczko, J. L., Stryer, L., Berg, J. M., Tymoczko, J. L., & Stryer, L. (2002). Biochemistry (5th ed.). W H Freeman. Section 8.4 The Michaelis-Menten Model Accounts for the Kinetic Properties of Many Enzymes.) than OptiPhos and Quantum Blue 5G at the pH range of 2-4.

TABLE 8 shows all kinetic parameters (Vmax, Km, Kcat and Kcat/Km) determined for the purified phytases at different pH values:

| pH | 2 | 2.5 | 3 | 3.5 | 4 |
|---|---|---|---|---|---|
| appA2C, MW=50.9kDa | | | | | |
| $V_{max}$/mg, mkmole/(min × mg) | 900 | 1060 | 1260 | 1280 | 1190 |
| $K_m$, mM | 0.313 | 0.412 | 0.463 | 0.443 | 0.461 |
| $k_{cat}$, sec$^{-1}$ | 764 | 895 | 1070 | 1090 | 1010 |
| $k_{cat}/K_m$, (sec$^{-1}$ M$^{-1}$) × 10$^4$ | 244 | 217 | 232 | 246 | 219 |
| PhOP-0136, MW = 69.1 kDa | | | | | |
| $V_{max}$/mg, mkmole/(min × mg) | 914 | 1400 | 2210 | 3640 | 3210 |
| $K_m$, mM | 0.387 | 0.693 | 1.12 | 1.79 | 1.69 |
| $k_{cat}$, sec$^{-1}$ | 1050 | 1610 | 2550 | 4200 | 3700 |
| $k_{cat}/K_m$, (sec$^{-1}$ M$^{-1}$) × 10$^4$ | 272 | 233 | 228 | 234 | 219 |
| PhOP-0142, MW = 70.5 kDa | | | | | |
| $V_{max}$/mg, mkmole/(min × mg) | 554 | 892 | 1140 | 1110 | 1020 |
| $K_m$, mM | 0.23 | 0.405 | 0.479 | 0.465 | 0.458 |
| $k_{cat}$, sec$^{-1}$ | 651 | 1050 | 1340 | 1300 | 1190 |
| $k_{cat}/K_m$, (sec$^{-1}$ M$^{-1}$) × 10$^4$ | 283 | 259 | 279 | 280 | 261 |
| PhOP-0161, MW = 71.9 kDa | | | | | |
| $V_{max}$/mg, mkmole/(min × mg) | 509 | 670 | 821 | 893 | 1040 |
| $K_m$, mM | 0.207 | 0.257 | 0.314 | 0.318 | 0.434 |
| $k_{cat}$, sec$^{-1}$ | 610 | 803 | 984 | 1070 | 1240 |
| $k_{cat}/K_m$, (sec$^{-1}$ M$^{-1}$) × 10$^4$ | 295 | 312 | 314 | 337 | 286 |
| PhOP-0175, MW = 69.1 kDa | | | | | |
| $V_{max}$/mg, mkmole/(min × mg) | 605 | 658 | 937 | 1110 | 1050 |
| $K_m$, mM | 0.39 | 0.452 | 0.6 | 0.702 | 0.702 |
| $k_{cat}$, sec$^{-1}$ | 697 | 758 | 1080 | 1270 | 1210 |
| $k_{cat}/K_m$, (sec$^{-1}$ M$^{-1}$) × 10$^4$ | 179 | 168 | 180 | 181 | 173 |
| Quantum Blue 5 G, MW = 47.8 kDa | | | | | |
| $V_{max}$/mg, mkmole/(min × mg) | 591 | 635 | 889 | 914 | 889 |
| $K_m$, mM | 0.389 | 0.424 | 0.591 | 0.612 | 0.562 |
| $k_{cat}$, sec$^{-1}$ | 471 | 506 | 709 | 728 | 709 |
| $k_{cat}/K_m$, (sec$^{-1}$ M$^{-1}$) × 10$^4$ | 121 | 119 | 120 | 119 | 126 |

5. Pelletizing Test

Thermal Stability of OptiPhos, Quantum Blue and four enzymes of the present invention was tested in a pelletizing experiment. This test shows the practical relevance of the improved thermostability of the enzymes of the present invention as opposed to OptiPhos and Quantum blue. In pelletizing feed under high temperatures of 80 and 90° C. for about 1 min, the enzymes of the present invention were more stable than OptiPhos and Quantum blue. Data of this experiment are shown in FIG. 6.

Batches of broiler feed were pelletized with steam conditioning at 80 and 90° C. Broiler feed was delivered by Cibus NV. 200,00 g enzyme were mixed with 200 kg of broiler feed in a vertical screw mixer. After 15 minutes of mixing the feed was pelletized on a Labor Monoroll Pellet mill with a 4×50 mm die with steam conditioning at different temperatures.

The pellets were cooled Immediately after pelletizing with a forced air cooler at ambient air temperature.

Figure 6:
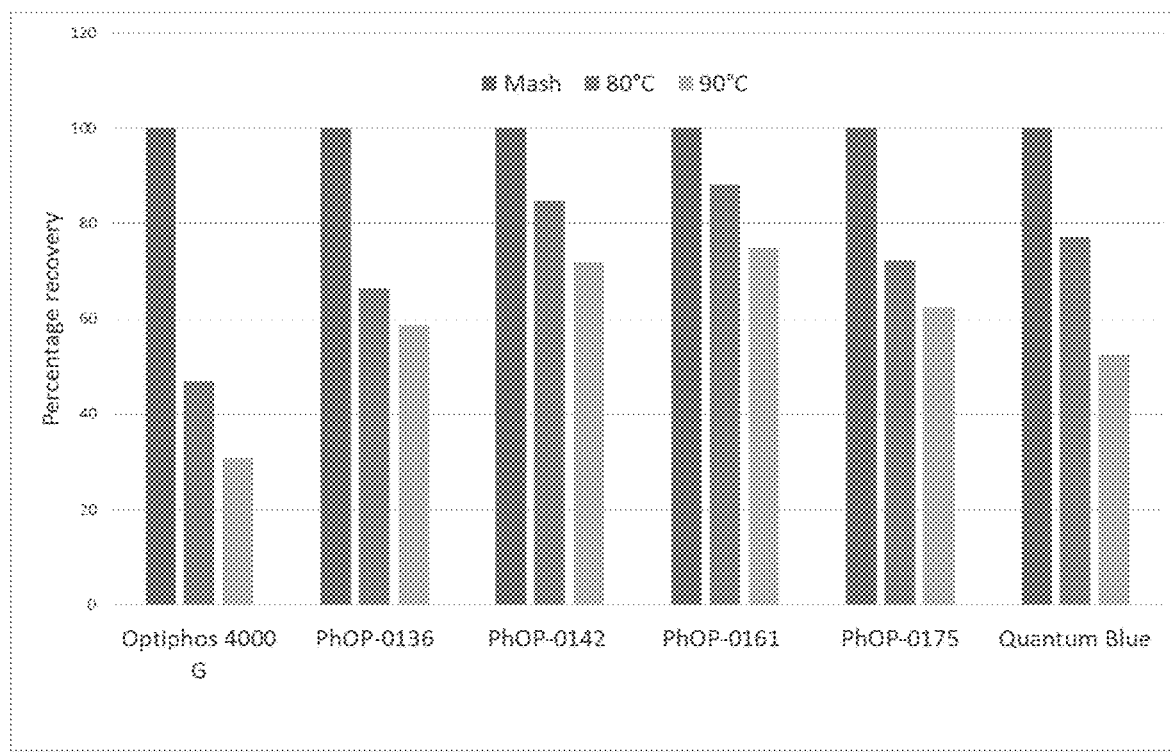
FIG. 6 shows the percentage recovery of active enzyme in phytase activity units after pelletizing compared to mash, i.e. before pelletizing. Higher amounts of PhOP-0136, PhOP-0142, PhOP-0161 and PhOP-0175 were obtained at both 80° C. and 90° C. as compared to OptiPhos and at 90° C. as compared to Quantum blue

FIG. 6 shows the percentage recovery of active enzyme (determined by activity assay ISO30024:2009) after pelletizing compared to mash, i.e. before pelletizing. Higher amounts of PhOP-0136, PhOP-0142, PhOP-0161 and PhOP-0175 were obtained at both 80° C. and 90° C. as compared to OptiPhos and at 90° C. as compared to Quantum blue.

6. Feed Efficacy Tests

In a trial of the University of Warmia and Maszury, Poland the effect of the new phytases PhOP-0136 and PhOP-0161 was tested and compared to OptiPhos on ROSS 308 male chickens.

The aim of the study was to evaluate the effect of different phytases on the performance parameters such as weight gain and bone mineralization as indication of phosphate incorporation. In total of 1056 healthy day old male Ross 308 broilers (Gallus gallus) were split into eight treatment groups (T1-8):

T1—Positive control (sufficient in P)
T2—Negative control (reduced in P)
T3—Negative control+PhOP-0136-250 FTU/kg
T4—Negative control+PhOP-0136-500 FTU/kg
T5—Negative control+PhOP-0161-250 FTU/kg
T6—Negative control+PhOP-0161-500 FTU/kg
T7—Negative control+PhOP-0175-250 FTU/kg
T8—Negative control+TSP 175-500 FTU/kg The birds were kept in floor pens—96 pens in total, 0.7 m$^2$ each. Every treatment group had 12 pens (replicates) in each, 11 birds in each pen—132 birds per treatment group. The length of rearing period was 35 days. The birds were sexed at the hatchery to ensure only males were selected and after transporting to the farm randomly distributed to the separate treatments and replicates. The trial ran in a common poultry house with artificial lightening program, automated gas heating and forced ventilation. The heating program was conducted according the recommendations of Ross (Ross Manual (2014): www.aviagen.com). From day 1 to day 3 the temperature was about 29-30° C., then slowly decreased to reach 21° C. at day 21 and this temperature was kept at 21° C. till the end of the study. The humidity was between 65-70% till day 9 and then between 60-70% till the end of experiment. Feed and water were supplied ad libitum.

Test materials were 6-phytase preparations produced by the Huvepharma: PhOP-0136, PhOP-0161 and OptiPhos. For all three phytases, each time two premixes were provided, pre-diluted with carrier (wheat flour) to achieve a concentration in the feed of respectively 250 FTU/kg and 500 FTU/kg when added at to the feed at 500 g/ton. Levels of the added phytase in the feed were verified using ISO30024:2009 method.

The phytase activity in phytases pre-diluted with carrier (wheat flour) of the different treatments and the batch number of the corresponding phytase product is shown below:

| Experimental name | Phytase activity | Batch n° |
|---|---|---|
| TR3-PhOP136-250 FTU | 590 FTU/g | 17121274157 |
| TR4-PhOP-0136-500 FTU | 1050 FTU/g | 17121274158 |
| TR5-PhOP-0161-250 FTU | 640 FTU/g | 17121274159 |
| TR6-PhOP-0161-500 FTU | 1190 FTU/g | 17121274160 |
| TR7-PhOP-0175-250 FTU | 600 FTU/g | 17121274161 |
| TR8-PhOP-0175-500 FTU | 1100 FTU/g | 17121724162 |

The basal feed mixtures were prepared in the feed mill Research Diet Services, The Netherlands. The mixtures were pelleted at 70° C. The composition and nutritional value of basal feed mixtures is shown in tables 9 and 10. To avoid health problems in the negative control group (T2) due to insufficient phosphorus in the diet, the birds from all treatments received the same starter diet till day 5 that met the nutritional requirements of a broiler chick. (Table 9). The positive control feed mixtures was the experimental diet for group T1, and the negative control feed mixture for groups for T2 to T8. Diets were formulated in such way to obtain a difference in available phosphorous between negative and the positive control diet of approximately 1.5 g/kg. The experimental diets for T3-T8 were prepared by using the negative control diet mixture and adding the respective phytase preparations.

During the rearing period feed phases in pelleted form were used:

1-5 days—starter diet (same for all treatments)

6-21 days—grower diet 22-35 days—finisher diet

The composition of the diets is shown in tables 9 and 10

TABLE 9

Composition of the positive control diets, %

| Compounds | Starter (1-5 days) | Grower (6-21 days) | Finisher (22-35 days) |
|---|---|---|---|
| Corn | 36.18 | 57.00 | 54.59 |
| Wheat | 25.00 | — | — |
| Soybean meal | 31.50 | 25.20 | 19.60 |
| Rapeseed meal | — | 10.00 | 15.00 |
| Animal fat (lard) | — | 3.00 | 4.00 |
| Soybean oil | 2.90 | 1.40 | 2.55 |
| Na-Bicarbonate | 0.26 | 0.21 | 0.20 |
| Salt | 0.21 | 0.22 | 0.20 |
| Limestone | 1.39 | 1.11 | 0.97 |
| MCP | 1.56 | 0.98 | 0.84 |
| DL-Methionine | 0.24 | 0.18 | 0.19 |
| L-Lysine | 0.18 | 0.17 | 0.26 |
| L-Threonine | 0.06 | 0.03 | 0.06 |
| L-Valine | 0.03 | — | 0.05 |
| TiO$_2$ | — | — | 1.00 |
| Premix (corn) | 0.50 | 0.50 | 0.50 |
| Nutrients density | | | |
| ME (kcal/kg) | 2851 | 2902 | 2951 |
| Crude protein (g/kg) | 214.80 | 204.80 | 193.50 |
| Crude fibre (g/kg) | 24.20 | 31.10 | 34.50 |
| Crude fat (g/kg) | 52.20 | 74.20 | 95.00 |
| Crude ash (g/kg) | 60.90 | 54.50 | 61.40 |
| Dig. Lysine (g/kg) | 10.99 | 10.32 | 10.22 |
| Dig. Methionine (g/kg) | 5.15 | 4.69 | 4.69 |
| Dig. Met. + Cys (g/kg) | 8.04 | 7.53 | 7.46 |
| Dig. Threonine (g/kg) | 7.13 | 6.75 | 6.65 |
| Dig. Valine (g/kg) | 8.78 | 8.25 | 8.14 |
| Calcium (g/kg) | 9.00 | 7.50 | 7.00 |
| Total Phosphorus (g/kg) | 7.10 | 6.30 | 6.00 |
| Av. Phosphorus (g/kg) | 4.49 | 3.41 | 3.10 |

TABLE 10

Composition of the negative control diets, %

| Compounds | Starter (1-5 days) | Grower (6-21 days) | Finisher (22-35 days) |
|---|---|---|---|
| Corn | | 58.27 | 55.80 |
| Wheat | | — | — |
| Soybean meal | | 25.20 | 19.40 |
| Rapeseed meal | | 10.00 | 15.00 |
| Animal fat (lard) | | 3.00 | 4.00 |
| Soybean oil | | 0.95 | 2.15 |
| Na-Bicarbonate | | 0.21 | 0.20 |
| Salt | | 0.22 | 0.20 |
| Limestone | | 1.16 | 1.02 |
| MCP | | 0.31 | 0.18 |
| DL-Methionine | | 0.18 | 0.19 |
| L-Lysine | | 0.18 | 0.26 |
| L-Threonine | | 0.03 | 0.06 |
| L-Valine | | — | 0.05 |
| TiO$_2$ | | — | 1.00 |
| Premix (corn) | | 0.50 | 0.50 |
| Nutrients density | | | |
| ME (kcal/kg) | | 2901 | 2952 |
| Crude protein (g/kg) | | 204.90 | 193.50 |
| Crude fibre (g/kg) | | 31.20 | 34.60 |
| Crude fat (g/kg) | | 70.30 | 91.50 |
| Crude ash (g/kg) | | 48.40 | 55.40 |
| Dig. Lysine (g/kg) | | 10.32 | 10.18 |
| Dig. Methionine (g/kg) | | 4.69 | 4.70 |
| Dig. Met. + Cys (g/kg) | | 7.55 | 7.47 |
| Dig. Threonine (g/kg) | | 6.74 | 6.64 |
| Dig. Valine (g/kg) | | 8.25 | 8.13 |
| Calcium (g/kg) | | 6.50 | 6.00 |
| Total Phosphorus (g/kg) | | 4.80 | 4.60 |
| Av. Phosphorus (g/kg) | | 1.91 | 1.62 |

Measurements

Below, the following abbreviations will be used

| Abbreviation | Meaning |
|---|---|
| BW | Body Weight |
| FI | Feed Intake |
| FCR | Feed Conversion Rate |
| ADG | Average Daily Gain |
| ADFI | Average Daily Feed Intake |

Body weight (BW) of broilers (pen basis) was measured at days 1, 5, 21 and 35. Feed consumption (feed intake, FI) was measured for experimental periods: 1-5, 6-21, 22-35 and 1-35 days. For bone ash analyses: 2 birds from each pen with average weight were taken in age of 21 days, then the right tibias were removed and both samples pooled. The samples were analyzed for percentage of ash content and the ash residue stored separate for further analysis if needed.

The study schedule was as follows:

| d1-d5 | 12 Dec. 2017-16 Dec. 2017 | all chickens on positive control starter diet containing sufficient P level |
|---|---|---|
| d5 | 17 Dec. 2017 | BW, FI, FCR + switch to grower according to respective treatments |
| d21 | 2 Jan. 2018 | BW, FI, FCR + tibia ash (2 chickens/pen) + switch to finisher (with marker) |
| d31-d33 | 12 Jan. 2018-14 Jan. 2018 | 3 days of fecal sampling |
| d35 | 16 Jan. 2018 | End of study-BW, FI, FCR |

6.1 Growth Performance During Starting Period (1-5 Days)

At start of the experiment the average body weight of day-old chickens was 38.9 g. During the starter period (1-5 days) the birds consumed in average 121.0 g of feed per bird and the average feed conversion ratio was 1.100 kg/kg. During this period, all treatment groups received the same starter diet.

6.2 Body Weight (BW) and Average Daily Gain (ADG)

After weighing at day 5 the replicates were exchanged between treatments when needed to reach the same average body weight in all treatment groups before start of the main experiment. There were significant differences in body weight (BW) at the end of the grower period (day 21) between treatments. The birds from the PC group (T1) were significantly heavier than those from NC group (T2) and all phytase supplemented groups, the only exception being birds of T6 (PhOP-161 at 500 FTU/kg feed) who had a similar weight as the PC. Also the addition of phytase preparations in treatments T3-T8 significantly improved body weight and average daily gain (ADG) compared to NC group (T2) by the end of the grower period. During the finisher period (22-35 days) the ADG of PC birds and those from all phytase treatments (except T3—only near significant trend, P=0.074) was significantly higher than in NC treatment (T2). The body weight at the end of experiment (day 35) and ADG for the entire experiment (6-35 days) were significantly higher in PC (T1, 10.80%) and all phytase treatments (from 7.70 in T7 to 12.44% in T6) than the birds from NC group (T2). Birds from all phytase treatments showed similar final BW and ADG over the test period as each other and the PC. The final body weight in all treatment groups (except NC-T2) was higher than Ross 308 standards (2.283 kg).

6.3 Average Daily Feed Intake (ADFI)

Overall, there were near-significant differences in average daily feed intake between treatments during the grower period (6-21 days; P=0.055) and the entire experimental period (6-35 days; P=0.070), The birds from T5 (PhOP-161-250 FTU/kg) & T6 (PhOP-161-500 FTU/kg) tended to consume more feed (0.05<p<0.10) than those from NC (T2) treatment during the grower period. For the entire experiment the T6 birds tended to consume more feed than the NC birds (T2). During the finisher period (22-35 days) there was a significant effect of treatment on average daily feed intake. Birds from T5 (PhOP-161-250 FTU/kg) & T6 (PhOP-161-500 FTU/kg) consumed significantly more feed than the NC (T2) birds and additionally T6 birds consumed significantly more than T3 (PhOP-136-250 FTU/kg) birds.

6.4 Feed Conversion Ratio (FCR)

There were significant differences in FCR during grower period (6-21 days) between treatments. The birds of T2 (NC)—showed numerically the worst FCR, and the PC birds (T1) and the birds of T6 (PhOP-161 at 500 FTU/kg) significantly better converted feed than those from NC group (T2). T5 (PhOP-161-250 FTU/kg) & T7 (OptiPhos—250 FTU/kg) were the only phytase treatments that had a FCR that was significantly worse than the PC (T1). During the finisher period (22-35 days) the FCR values of PC birds and of birds from all phytase treatments (except T6—only near significant trend, P=0.051) were significantly lower than in NC treatment (T2).

During the entire experiment (6-35 days) the FCR for PC birds (T1) was significantly better than for birds from NC group (T2) and T7 (OptiPhos—250 FTU/kg) (-6.49% and -2.86%, respectively). Birds from all phytase supplemented treatments (T3-T8) significantly improved FCR (from -3.73% to -6.13% in T7 and T8, respectively) compared to NC group (T2). Birds from T3-T6 and T8 showed a similar FCR as the T1 (PC) birds.

6.5 Tibia Ash

The decrease of available Ca and P levels in the diets for negative control birds (T2) resulted in significantly lower tibia ash content compared with positive control birds (T1). The birds from all phytase treatments (T3-T8) were characterized by significantly higher tibia ash content compared to negative control birds (T2). Birds from T6 (PhOP-161-500 FTU/kg) and T8 (OptiPhos—500 FTU/kg) had similar tibia ash content as the T1 (PC) birds.

6.6 Conclusions

The addition of different phytase preparations at 250 and 500 FTU/kg to the NC diet had a significant positive effect on:

1) the BW and ADWG of birds from all phytase supplemented groups (T3-T8) over the experimental period,
2) the FCR of birds from all phytase supplemented groups,
3) the tibia ash from all phytase supplemented groups, Data are shown in tables 11 to 13 below and in FIGS. 7 and 8. Overall, PhOP-161 turned out to be most promising in all experiments (BW, ADG, FCR and tibia ash). Also PhOP-136 showed excellent performance in all experiments resembling the data of commercial OptiPhos.

The data show that the new phytase variants provided in this invention release available phosphorous from feeding stuffs and provide excellent broiler growth performance parameters, such as bone mineralization, BW, ADG and FCR.

TABLE 11 shows the average daily weight gain (ADG, in g) of chicken, determined for the a purified phytases between days 5 and 21, days 21 and 35 and on day 35. Values within column with different superscript are significantly different at $P < 0.05$:

| Tr | Product | Target phytase level (FTU/kg) | d5-21 | d21-35 | d5-35 |
|---|---|---|---|---|---|
| 1 | Positive control | 0 | 53.1$^a$ | 96.6$^a$ | 73.4$^a$ |
| 2 | Negative control | 0 | 46.0$^d$ | 88.2$^b$ | 65.7$^c$ |
| 3 | PhOP-0136 | 250 | 49.8b$^c$ | 95.5$^a$ | 71.1$^b$ |
| 4 | PhOP-0136 | 500 | 50.7$^b$ | 97.2$^a$ | 72.4$^{ab}$ |
| 5 | PhOP-0161 | 250 | 50.5$^{bc}$ | 99.2$^a$ | 73.2$^{ab}$ |
| 6 | PhOP-0161 | 500 | 52.3$^a$ | 99.9$^a$ | 74.5$^a$ |
| 7 | OptiPhos | 250 | 49.0$^c$ | 96.4$^a$ | 71.1$^b$ |
| 8 | OptiPhos | 500 | 50.7$^b$ | 99.2$^a$ | 73.3$^{ab}$ |

TABLE 12 shows the feed conversion rate (FCR, in kg/kg) of chicken, determined for purified phytases on day 5, between days 21 and 35 and between days 5 and 35. Values within a column with different superscript are significantly different at P < 0.05.

| Tr | Product | Target phytase level (FTU/kg) | d5-21 | d21-35 | d5-35 |
|---|---|---|---|---|---|
| 1 | Positive control | 0 | 1.306$^a$ | 1.616$^a$ | 1.479$^a$ |
| 2 | Negative control | 0 | 1.436$^c$ | 1.691$^b$ | 1.582$^d$ |
| 3 | PhOP-0136 | 250 | 1.364$^{ab}$ | 1.589$^a$ | 1.491$^{ab}$ |
| 4 | PhOP-0136 | 500 | 1.358$^{ab}$ | 1.604$^a$ | 1.498$^{abc}$ |
| 5 | PhOP-0161 | 250 | 1.389$^{bc}$ | 1.607$^a$ | 1.516$^{bc}$ |
| 6 | PhOP-0161 | 500 | 1.350$^{ab}$ | 1.624$^a$ | 1.506$^{abc}$ |
| 7 | OptiPhos | 250 | 1.400$^{bc}$ | 1.613$^a$ | 1.523$^c$ |
| 8 | OptiPhos | 500 | 1.356$^{ab}$ | 1.580$^a$ | 1.485$^a$ |

Figure 7:
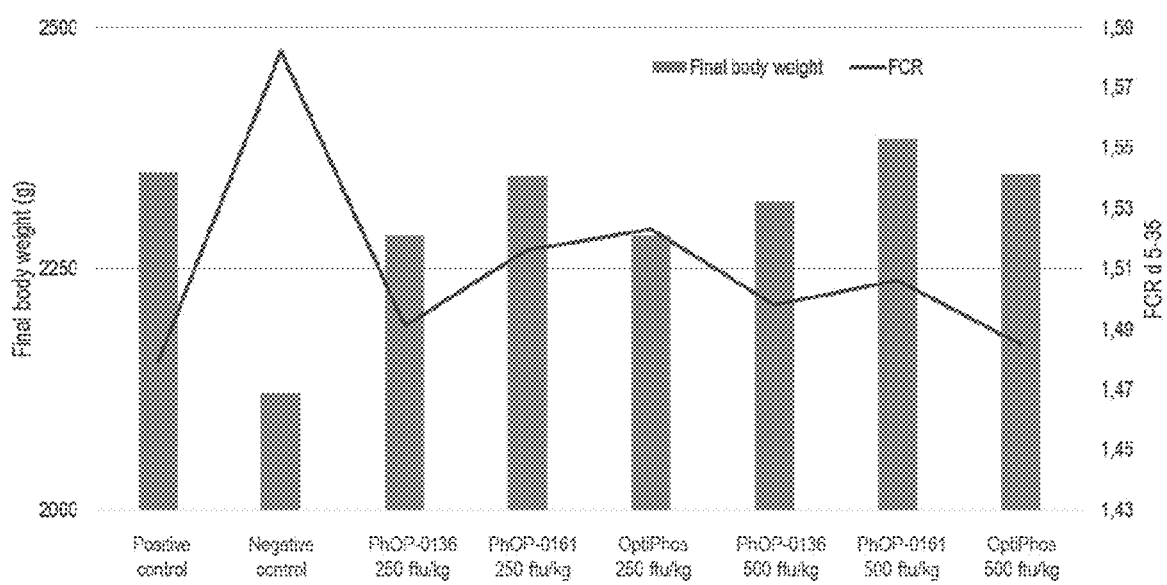
FIG. 7 shows the effects of different phytases on the growth performance of broilers. Final body weight and FCR at day 35. PhOP-136 and PhOP-161 showed excellent performance, in parts better than OptiPhos.

The data of Table 12 are also shown in FIG. 7.

TABLE 13 shows the percentage of ash content in tibia bone of of the different tratments at day 35. Values within a column with different superscript are significantly different at P < 0.05:

| Tr | Product | Target phytase level (FTU/kg) | Ash content, % |
|---|---|---|---|
| 1 | Positive control | 0 | 47.4$^a$ |
| 2 | Negative control | 0 | 40.9$^d$ |
| 3 | PhOP-0136 | 250 | 45.1$^c$ |
| 4 | PhOP-0136 | 500 | 45.4$^c$ |
| 5 | PhOP-0161 | 250 | 45.0$^c$ |
| 6 | PhOP-0161 | 500 | 47.1$^{ab}$ |
| 7 | OptiPhos | 250 | 44.6$^c$ |
| 8 | OptiPhos | 500 | 45.9$^{bc}$ |

Figure 8:
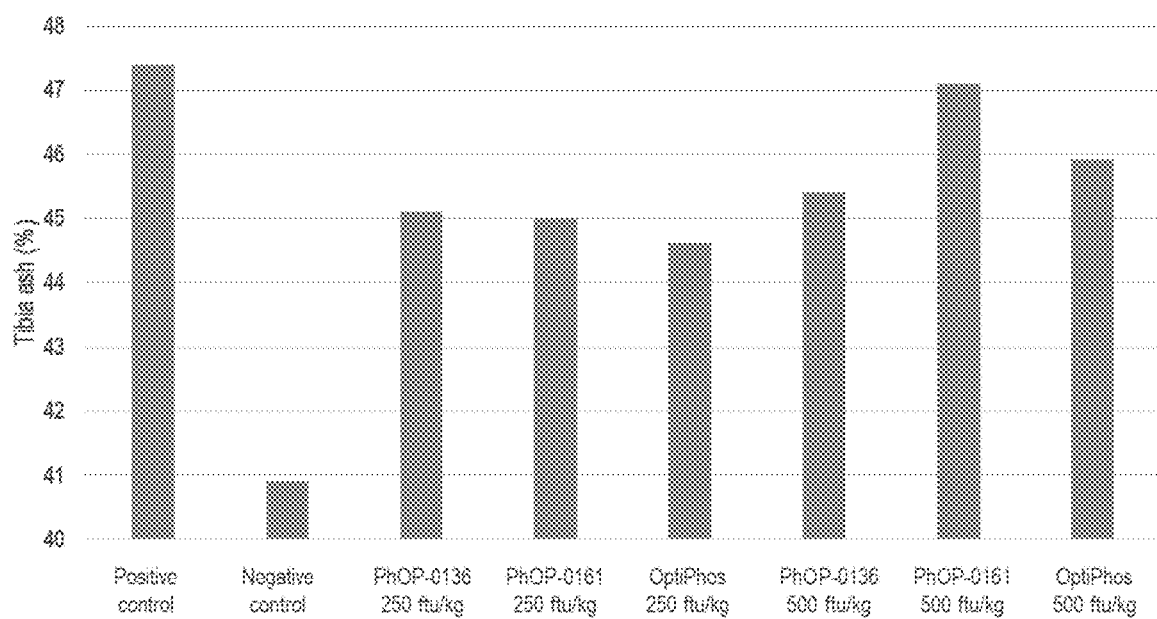
FIG. 8 shows the effects of different phytases on bone mineralization of broiler chickens. Tibia ash data at 21 days. PhOP-161 showed excellent performance, better than OptiPhos.

The data of Table 13 are also shown in FIG. 8.

7. Summary

Starting point of engineering phytase of the invention was the phytase variant PhOP-0093, whose thermostability was already improved by 20° C. compared to OptiPhos phytase. The further improvement of thermostability succeeded quite well. Mutagenesis and screening in *E. coli* resulted in improvements by up to 3° C. to PhOP-0093. Recombination of the beneficial mutations lead to further, distinctly enhanced stabilities of 8-10° C. over PhOP-0093. The transfer of these stability improvements from screening host *E. coli* to final production host *Pichia pastoris* was accomplished well and again enhanced by glycosylation effects.

Achieved overall thermostability improvements of PhOP-variants over those from commercial phytases are between 24.5 to 33° C. (OptiPhos) and 1.5 to 10° C. (Quantum Blue 5G).

Final variants carry 16-18 mutations compared to sequence appA2C (PhOP-wt):

TABLE 14

Overview of mutations in preferred mutants

| | Position (*) | | | | | | | | | | | | | | | | | |
|---|---|---|---|---|---|---|---|---|---|---|---|---|---|---|---|---|---|---|
| | 26 | 57 | 84 | 95 | 129 | 159 | 161 | 179 | 181 | 198 | 201 | 207 | 233 | 249 | 275 | 277 | 309 | 349 |
| PhOP-wt (AppA2c) | P | D | Q | A | D | N | N | G | R | N | L | D | V | Q | Q | Y | Q | T |
| PhOP-0093 | E | D | W | A | D | V | N | G | Y | N | L | N | W | Q | Q | D | Q | Y |
| PhOP-0136 | E | Y | W | P | G | V | R | G | Y | P | K | N | W | E | Y | D | S | Y |
| PhOP-0138 | E | Y | W | P | G | V | R | N | Y | P | K | N | W | Q | Y | D | S | Y |
| PhOP-0142 | E | Y | W | P | D | V | R | N | Y | P | K | N | W | E | Y | D | Q | Y |
| PhOP-0161 | E | Y | W | P | D | V | N | S | Y | P | K | N | W | E | Y | D | S | Y |
| PhOP-0169 | E | Y | W | A | G | V | R | S | Y | P | K | N | W | E | Y | D | S | Y |
| PhOP-0175 | E | Y | W | P | D | V | R | N | Y | N | K | N | W | E | Y | D | S | Y |
| PhOP-0176 | E | D | W | P | G | V | R | N | Y | P | K | N | W | Q | Y | D | S | Y |
| PhOP-0179 | E | Y | W | P | G | V | R | N | Y | P | L | N | W | E | Y | D | S | Y |
| PhOP-0180 | E | Y | W | P | G | V | R | N | Y | P | K | N | W | E | Y | D | S | Y |

The invention claimed is:

1. A mutant phytase, comprising the amino acid sequence of SEQ ID NO: 2 with mutations E4, W62, V137, Y159, N185, W211, D255 and Y327, wherein the mutant phytase has phytase activity.

2. The mutant phytase of claim 1, wherein the phytase is expressed in a fungal host cell.

3. The mutant phytase of claim 1, wherein the phytase is expressed in a bacterial host.

4. The mutant phytase of claim 1, wherein the phytase exhibits a thermostability of 50% at 79.5° C. when expressed in *Escherichia coli*.

5. The mutant phytase of claim 1, wherein the phytase exhibits a thermostability of 50% at 86° C. when expressed in *Pichia pastoris*.

6. The mutant phytase of claim 1, wherein the phytase exhibits a thermostability of 50% at 95° C.

7. The mutant phytase of claim 1, wherein the amino acid sequence has at least 98% sequence identity with SEQ ID NO: 2.

8. The mutant phytase of claim 7, wherein the phytase is expressed in a fungal host.

9. The mutant phytase of claim 7, wherein the phytase is expressed in a bacterial host.

10. The mutant phytase of claim 7, wherein the phytase exhibits a thermostability of 50% at 79.5° C. when expressed in *Escherichia coli*.

11. The mutant phytase of claim 7, wherein the phytase exhibits a thermostability of 50% at 86° C. when expressed in *Pichia pastoris*.

12. The mutant phytase of claim 7, wherein the phytase exhibits a thermostability of 50% at 95° C.

13. A mutant phytase, comprising the amino acid sequence of SEQ ID NO: 2 with mutations E4, W62, V137, Y159, N185, W211, D255 and Y327, and further comprising one or more additional mutations at positions selected from the group consisting of: 35, 73, 107, 139, 157, 176, 179, 227, 253 and 287 in SEQ ID NO: 2, wherein the mutant phytase has phytase activity.

14. The mutant phytase of claim 13, wherein the one or more additional mutations are selected from 35Y, 73P, 107G, 139R, 157R/S/N, 176P, 179K, 227E, 253Y and 287S in SEQ ID NO: 2.

15. The mutant phytase of claim 14, wherein the phytase is expressed in a fungal host.

16. The mutant phytase of claim 14, wherein the phytase is expressed in a bacterial host.

17. The mutant phytase of claim 14, wherein the phytase exhibits a thermostability of 50% at 79.5° C. when expressed in *Escherichia coli*.

18. The mutant phytase of claim 14, wherein the phytase exhibits a thermostability of 50% at 86° C. when expressed in *Pichia pastoris*.

19. The mutant phytase of claim 14, wherein the phytase exhibits a thermostability of 50% at 95° C.

20. The mutant phytase of claim 13, wherein the phytase is expressed in a fungal host.

21. The mutant phytase of claim 13, wherein the phytase is expressed in a bacterial host.

22. The mutant phytase of claim 13, wherein the phytase exhibits a thermostability of 50% at 79.5° C. when expressed in *Escherichia coli*.

23. The mutant phytase of claim 13, wherein the phytase exhibits a thermostability of 50% at 86° C. when expressed in *Pichia pastoris*.

24. The mutant phytase of claim 13, wherein the phytase exhibits a thermostability of 50% at 95° C.

25. A mutant phytase, comprising the amino acid sequence of SEQ ID NO: 2 with mutations E4, W62, V137, Y159, N185, W211, D255 and Y327, and further comprising one or more additional mutations which are 25F, 43P, and/or 225Y, and wherein the mutant phytase has phytase activity.

26. The mutant phytase of claim 25, wherein the phytase is expressed in a fungal host.

27. The mutant phytase of claim 25, wherein the phytase is expressed in a bacterial host.

28. The mutant phytase of claim 25, wherein the phytase exhibits a thermostability of 50% at 79.5° C. when expressed in *Escherichia coli*.

29. The mutant phytase of claim 25, wherein the phytase exhibits a thermostability of 50% at 86° C. when expressed in *Pichia pastoris*.

30. The mutant phytase of claim 25, wherein the phytase exhibits a thermostability of 50% at 95° C.

* * * * *

SEQUENCE LISTING

<160> NUMBER OF SEQ ID NOS: 12

<210> SEQ ID NO 1
<211> LENGTH: 410
<212> TYPE: PRT
<213> ORGANISM: Artificial Sequence
<220> FEATURE:
<223> OTHER INFORMATION: Mature phytase variant starting from Q23; PhOP-wt (AppA2c)

<400> SEQUENCE: 1

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350
```

```
Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 2
<211> LENGTH: 410
<212> TYPE: PRT
<213> ORGANISM: Artificial Sequence
<220> FEATURE:
<223> OTHER INFORMATION: Mature phytase variant starting from Q23;
      PhOP-0093

<400> SEQUENCE: 2

Gln Ser Glu Glu Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Trp Arg Gln
    50                  55                  60

Arg Leu Val Ala Asp Gly Leu Leu Ala Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Val Ala Asn Val Thr Asp Ala Ile
    130                 135                 140

Leu Ser Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Asn Arg Glu Lys Gln Asn Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Trp Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300
```

```
Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Leu Val Phe Glu
            325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 3
<211> LENGTH: 410
<212> TYPE: PRT
<213> ORGANISM: Artificial Sequence
<220> FEATURE:
<223> OTHER INFORMATION: Mature phytase variant starting from Q23;
      PhOP-0136

<400> SEQUENCE: 3

Gln Ser Glu Glu Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Tyr Ala Trp Pro Thr Trp Pro Val Lys Leu Gly Trp Leu Thr
            35                  40                  45

Pro Arg Gly Gly Glu Leu Ile Ala Tyr Leu Gly His Tyr Trp Arg Gln
50                  55                  60

Arg Leu Val Ala Asp Gly Leu Leu Pro Lys Lys Gly Cys Pro Gln Pro
65                  70                  75                  80

Gly Gln Val Ala Ile Ile Ala Asp Val Asp Glu Arg Thr Arg Lys Thr
            85                  90                  95

Gly Glu Ala Phe Ala Ala Gly Leu Ala Pro Gly Cys Ala Ile Thr Val
            100                 105                 110

His Thr Gln Ala Asp Thr Ser Ser Pro Asp Pro Leu Phe Asn Pro Leu
            115                 120                 125

Lys Thr Gly Val Cys Gln Leu Asp Val Ala Arg Val Thr Asp Ala Ile
130                 135                 140

Leu Ser Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Pro
            165                 170                 175

Leu Cys Lys Asn Arg Glu Lys Gln Asn Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Trp Ser Leu Ala Ser Met Leu Thr Glu Ile Phe Leu Leu Gln
            210                 215                 220

Gln Ala Glu Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
```

```
                    245                 250                 255
Leu Gln Arg Thr Pro Glu Val Ala Arg Ser Arg Ala Thr Pro Leu Leu
                260                 265                 270

Asp Leu Ile Met Ala Ala Leu Thr Pro His Pro Pro Gln Lys Ser Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 4
<211> LENGTH: 410
<212> TYPE: PRT
<213> ORGANISM: Artificial Sequence
<220> FEATURE:
<223> OTHER INFORMATION: Mature phytase variant starting from Q23;
      PhOP-0138

<400> SEQUENCE: 4

Gln Ser Glu Glu Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Tyr Ala Trp Pro Thr Trp Pro Val Lys Leu Gly Trp Leu Thr
            35                  40                  45

Pro Arg Gly Gly Glu Leu Ile Ala Tyr Leu Gly His Tyr Trp Arg Gln
        50                  55                  60

Arg Leu Val Ala Asp Gly Leu Leu Pro Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Gly Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Val Ala Arg Val Thr Asp Ala Ile
    130                 135                 140

Leu Ser Arg Ala Gly Gly Ser Ile Ala Asp Phe Thr Asn His Tyr Gln
145                 150                 155                 160

Thr Ala Phe Arg Glu Leu Glu Arg Val Leu Asn Phe Pro Gln Ser Pro
                165                 170                 175

Leu Cys Lys Asn Arg Glu Lys Gln Asn Glu Ser Cys Ser Leu Thr Gln
            180                 185                 190
```

```
Ala Leu Pro Ser Glu Leu Lys Val Ser Ala Asp Asn Val Ser Leu Thr
            195                 200                 205

Gly Ala Trp Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Ser Ala
            275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 5
<211> LENGTH: 410
<212> TYPE: PRT
<213> ORGANISM: Artificial Sequence
<220> FEATURE:
<223> OTHER INFORMATION: Mature phytase variant starting from Q23;
      PhOP-0142

<400> SEQUENCE: 5

Gln Ser Glu Glu Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Tyr Ala Trp Pro Thr Trp Pro Val Lys Leu Gly Trp Leu Thr
        35                  40                  45

Pro Arg Gly Gly Glu Leu Ile Ala Tyr Leu Gly His Tyr Trp Arg Gln
    50                  55                  60

Arg Leu Val Ala Asp Gly Leu Leu Pro Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Val Ala Arg Val Thr Asp Ala Ile
    130                 135                 140
```

Leu Ser Arg Ala Gly Gly Ser Ile Ala Asp Phe Thr Asn His Tyr Gln
145                 150                 155                 160

Thr Ala Phe Arg Glu Leu Glu Arg Val Leu Asn Phe Pro Gln Ser Pro
            165                 170                 175

Leu Cys Lys Asn Arg Glu Lys Gln Asn Glu Ser Cys Ser Leu Thr Gln
        180                 185                 190

Ala Leu Pro Ser Glu Leu Lys Val Ser Ala Asp Asn Val Ser Leu Thr
    195                 200                 205

Gly Ala Trp Ser Leu Ala Ser Met Leu Thr Glu Ile Phe Leu Leu Gln
210                 215                 220

Gln Ala Glu Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
            245                 250                 255

Leu Gln Arg Thr Pro Glu Val Ala Arg Ser Arg Ala Thr Pro Leu Leu
        260                 265                 270

Asp Leu Ile Met Ala Ala Leu Thr Pro His Pro Pro Gln Lys Gln Ala
    275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Glu Leu Val Phe Glu
            325                 330                 335

Arg Trp Arg Arg Leu Ser Asp Asn Ser Gln Trp Ile Gln Val Ser Leu
        340                 345                 350

Val Phe Gln Thr Leu Gln Gln Met Arg Asp Lys Thr Pro Leu Ser Leu
    355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> SEQ ID NO 6
<211> LENGTH: 410
<212> TYPE: PRT
<213> ORGANISM: Artificial Sequence
<220> FEATURE:
<223> OTHER INFORMATION: Mature phytase variant starting from Q23;
      PhOP-0161

<400> SEQUENCE: 6

Gln Ser Glu Glu Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Tyr Ala Trp Pro Thr Trp Pro Val Lys Leu Gly Trp Leu Thr
        35                  40                  45

Pro Arg Gly Gly Glu Leu Ile Ala Tyr Leu Gly His Tyr Trp Arg Gln
    50                  55                  60

Arg Leu Val Ala Asp Gly Leu Leu Pro Lys Lys Gly Cys Pro Gln Pro
65                  70                  75                  80

Gly Gln Val Ala Ile Ile Ala Asp Val Asp Glu Arg Thr Arg Lys Thr

```
            85                  90                  95
Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
            115                 120                 125

Lys Thr Gly Val Cys Gln Leu Asp Val Ala Asn Val Thr Asp Ala Ile
130                 135                 140

Leu Ser Arg Ala Gly Gly Ser Ile Ala Asp Phe Thr Ser His Tyr Gln
145                 150                 155                 160

Thr Ala Phe Arg Glu Leu Glu Arg Val Leu Asn Phe Pro Gln Ser Pro
            165                 170                 175

Leu Cys Lys Asn Arg Glu Lys Gln Asn Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Trp Ser Leu Ala Ser Met Leu Thr Glu Ile Phe Leu Leu Gln
            210                 215                 220

Gln Ala Glu Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
            245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Ser Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Glu Leu Val Phe Glu
            325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> SEQ ID NO 7
<211> LENGTH: 410
<212> TYPE: PRT
<213> ORGANISM: Artificial Sequence
<220> FEATURE:
<223> OTHER INFORMATION: Mature phytase variant starting from Q23;
      PhOP-0169

<400> SEQUENCE: 7

Gln Ser Glu Glu Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30
```

Thr Pro Tyr Ala Trp Pro Thr Trp Pro Val Lys Leu Gly Trp Leu Thr
         35                  40                  45

Pro Arg Gly Gly Glu Leu Ile Ala Tyr Leu Gly His Tyr Trp Arg Gln
 50                  55                  60

Arg Leu Val Ala Asp Gly Leu Leu Ala Lys Lys Gly Cys Pro Gln Pro
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Gly Cys Ala Ile Thr Val
                100                 105                 110

His Thr Gln Ala Asp Thr Ser Ser Pro Asp Pro Leu Phe Asn Pro Leu
                115                 120                 125

Lys Thr Gly Val Cys Gln Leu Asp Val Ala Arg Val Thr Asp Ala Ile
130                 135                 140

Leu Ser Arg Ala Gly Gly Ser Ile Ala Asp Phe Thr Ser His Tyr Gln
145                 150                 155                 160

Thr Ala Phe Arg Glu Leu Glu Arg Val Leu Asn Phe Pro Gln Ser Pro
                165                 170                 175

Leu Cys Lys Asn Arg Glu Lys Gln Asn Glu Ser Cys Ser Leu Thr Gln
                180                 185                 190

Ala Leu Pro Ser Glu Leu Lys Val Ser Ala Asp Asn Val Ser Leu Thr
                195                 200                 205

Gly Ala Trp Ser Leu Ala Ser Met Leu Thr Glu Ile Phe Leu Leu Gln
                210                 215                 220

Gln Ala Glu Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
                245                 250                 255

Leu Gln Arg Thr Pro Glu Val Ala Arg Ser Arg Ala Thr Pro Leu Leu
                260                 265                 270

Asp Leu Ile Met Ala Ala Leu Thr Pro His Pro Gln Lys Ser Ala
                275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
                370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 8
<211> LENGTH: 410
<212> TYPE: PRT
<213> ORGANISM: Artificial Sequence
<220> FEATURE:
<223> OTHER INFORMATION: Mature phytase variant starting from Q23;

PhOP-0175

<400> SEQUENCE: 8

Gln Ser Glu Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Tyr Ala Trp Pro Thr Trp Pro Val Lys Leu Gly Trp Leu Thr
        35                  40                  45

Pro Arg Gly Gly Glu Leu Ile Ala Tyr Leu Gly His Tyr Trp Arg Gln
    50                  55                  60

Arg Leu Val Ala Asp Gly Leu Leu Pro Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Pro Asp Pro Leu Phe Asn Pro Leu
        115                 120                 125

Lys Thr Gly Val Cys Gln Leu Asp Val Ala Arg Val Thr Asp Ala Ile
    130                 135                 140

Leu Ser Arg Ala Gly Gly Ser Ile Ala Asp Phe Thr Asn His Tyr Gln
145                 150                 155                 160

Thr Ala Phe Arg Glu Leu Glu Arg Val Leu Asn Phe Pro Gln Ser Asn
                165                 170                 175

Leu Cys Lys Asn Arg Glu Lys Gln Asn Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Trp Ser Leu Ala Ser Met Leu Thr Glu Ile Phe Leu Leu Gln
    210                 215                 220

Gln Ala Glu Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Ser Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

```
Asn Glu Ala Arg Ile Pro Ala Cys Ser Leu
            405                 410

<210> SEQ ID NO 9
<211> LENGTH: 410
<212> TYPE: PRT
<213> ORGANISM: Artificial Sequence
<220> FEATURE:
<223> OTHER INFORMATION: Mature phytase variant starting from Q23;
      PhOP-0176

<400> SEQUENCE: 9

Gln Ser Glu Glu Leu Lys Leu Glu Ser Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Trp Arg Gln
        50                  55                  60

Arg Leu Val Ala Asp Gly Leu Leu Pro Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Gly Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Val Ala Arg Val Thr Asp Ala Ile
130                 135                 140

Leu Ser Arg Ala Gly Gly Ser Ile Ala Asp Phe Thr Asn His Tyr Gln
145                 150                 155                 160

Thr Ala Phe Arg Glu Leu Glu Arg Val Leu Asn Phe Pro Gln Ser Pro
                165                 170                 175

Leu Cys Lys Asn Arg Glu Lys Gln Asn Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Trp Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Ser Ala
        275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350
```

```
Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 10
<211> LENGTH: 410
<212> TYPE: PRT
<213> ORGANISM: Artificial Sequence
<220> FEATURE:
<223> OTHER INFORMATION: Mature phytase variant starting from Q23;
      PhOP-0179

<400> SEQUENCE: 10

Gln Ser Glu Glu Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Tyr Ala Trp Pro Thr Trp Pro Val Lys Leu Gly Trp Leu Thr
        35                  40                  45

Pro Arg Gly Gly Glu Leu Ile Ala Tyr Leu Gly His Tyr Trp Arg Gln
    50                  55                  60

Arg Leu Val Ala Asp Gly Leu Leu Pro Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Gly Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Val Ala Arg Val Thr Asp Ala Ile
    130                 135                 140

Leu Ser Arg Ala Gly Gly Ser Ile Ala Asp Phe Thr Asn His Tyr Gln
145                 150                 155                 160

Thr Ala Phe Arg Glu Leu Glu Arg Val Leu Asn Phe Pro Gln Ser Pro
                165                 170                 175

Leu Cys Leu Asn Arg Glu Lys Gln Asn Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Trp Ser Leu Ala Ser Met Leu Thr Glu Ile Phe Leu Leu Gln
    210                 215                 220

Gln Ala Glu Gly Met Pro Glu Pro Gly Trp Gly Arg Ile Thr Asp Ser
225                 230                 235                 240

His Gln Trp Asn Thr Leu Leu Ser Leu His Asn Ala Tyr Phe Asp Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Ser Ala
        275                 280                 285

Tyr Gly Val Thr Leu Pro Thr Ser Val Leu Phe Ile Ala Gly His Asp
```

```
            290                 295                 300
Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Met Arg Asp Lys Thr Pro Leu Ser Leu
                355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 11
<211> LENGTH: 410
<212> TYPE: PRT
<213> ORGANISM: Artificial Sequence
<220> FEATURE:
<223> OTHER INFORMATION: Mature phytase variant starting from Q23;
      PhOP-0180

<400> SEQUENCE: 11

Gln Ser Glu Glu Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Tyr Ala Trp Pro Thr Trp Pro Val Lys Leu Gly Trp Leu Thr
            35                  40                  45

Pro Arg Gly Gly Glu Leu Ile Ala Tyr Leu Gly His Tyr Trp Arg Gln
        50                  55                  60

Arg Leu Val Ala Asp Gly Leu Leu Pro Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Gly Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Val Ala Arg Val Thr Asp Ala Ile
130                 135                 140

Leu Ser Arg Ala Gly Gly Ser Ile Ala Asp Phe Thr Asn His Tyr Gln
145                 150                 155                 160

Thr Ala Phe Arg Glu Leu Glu Arg Val Leu Asn Phe Pro Gln Ser Pro
                165                 170                 175

Leu Cys Lys Asn Arg Glu Lys Gln Asn Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Trp Ser Leu Ala Ser Met Leu Thr Glu Ile Phe Leu Leu Gln
    210                 215                 220

Gln Ala Glu Gly Met Pro Glu Pro Gly Trp Gly Arg Ile Thr Asp Ser
225                 230                 235                 240
```

```
His Gln Trp Asn Thr Leu Leu Ser Leu His Asn Ala Tyr Phe Asp Leu
            245             250             255

Leu Gln Arg Thr Pro Glu Val Ala Arg Ser Arg Ala Thr Pro Leu Leu
            260             265             270

Asp Leu Ile Met Ala Ala Leu Thr Pro His Pro Pro Gln Lys Ser Ala
            275             280             285

Tyr Gly Val Thr Leu Pro Thr Ser Val Leu Phe Ile Ala Gly His Asp
            290             295             300

Thr Asn Leu Ala Asn Leu Gly Gly Ala Leu Glu Leu Asn Trp Thr Leu
305             310             315             320

Pro Gly Gln Pro Asp Asn Tyr Pro Pro Gly Gly Glu Leu Val Phe Glu
            325             330             335

Arg Trp Arg Arg Leu Ser Asp Asn Ser Gln Trp Ile Gln Val Ser Leu
            340             345             350

Val Phe Gln Thr Leu Gln Gln Met Arg Asp Lys Thr Pro Leu Ser Leu
            355             360             365

Asn Thr Pro Pro Gly Glu Val Lys Leu Thr Leu Ala Gly Cys Glu Glu
            370             375             380

Arg Asn Ala Gln Gly Met Cys Ser Leu Ala Gly Phe Thr Gln Ile Val
385             390             395             400

Asn Glu Ala Arg Ile Pro Ala Cys Ser Leu
            405             410

<210> SEQ ID NO 12
<211> LENGTH: 22
<212> TYPE: PRT
<213> ORGANISM: Artificial Sequence
<220> FEATURE:
<223> OTHER INFORMATION: Native periplasmic leader peptide from AppA2c
      (E. coli)

<400> SEQUENCE: 12

Met Lys Ala Ile Leu Ile Pro Phe Leu Ser Leu Leu Ile Pro Leu Thr
1               5                   10                  15

Pro Gln Ser Ala Phe Ala
            20
```